(12) United States Patent
Rizvi

(10) Patent No.: US 6,168,611 B1
(45) Date of Patent: Jan. 2, 2001

(54) SUTURING NEEDLE ASSEMBLIES AND METHODS OF USE THEREOF

(76) Inventor: Syed Rizvi, 6208 Castle Cary Dr., Bakersfield, CA (US) 93306

(*) Notice: Under 35 U.S.C. 154(b), the term of this patent shall be extended for 0 days.

(21) Appl. No.: 09/391,442

(22) Filed: Sep. 8, 1999

(51) Int. Cl.[7] ............................................. A61B 17/06
(52) U.S. Cl. ............................................................ 606/222
(58) Field of Search .................................... 606/223, 222, 606/119, 167; 604/272, 19, 27, 264; 600/29; 128/898

(56) References Cited

U.S. PATENT DOCUMENTS

| | | | |
|---|---|---|---|
| 5,059,207 | * 10/1991 | Shah | 606/223 |
| 5,149,329 | 9/1992 | Richardson. | |
| 5,501,692 | * 3/1996 | Riza | 606/148 |
| 5,725,555 | * 3/1998 | Moll | 606/223 |
| 5,816,258 | 10/1998 | Jervis. | |
| 5,860,425 | 1/1999 | Benderev et al. . | |

FOREIGN PATENT DOCUMENTS

1718912 A1   3/1992  (SU) .

* cited by examiner

*Primary Examiner*—Michael Buiz
*Assistant Examiner*—(Jackie) Tan-Uyen T. Ho
(74) *Attorney, Agent, or Firm*—Donald A. Kettlestrings

(57) ABSTRACT

A suturing needle assembly enables simultaneous passage of suture and introduction of local anesthetic into body tissue. Two suturing needle assembly embodiments are described and methods of using the needle assemblies include cystopexy, cystourethropexy, urethropexy and uteropexy procedures.

16 Claims, 23 Drawing Sheets

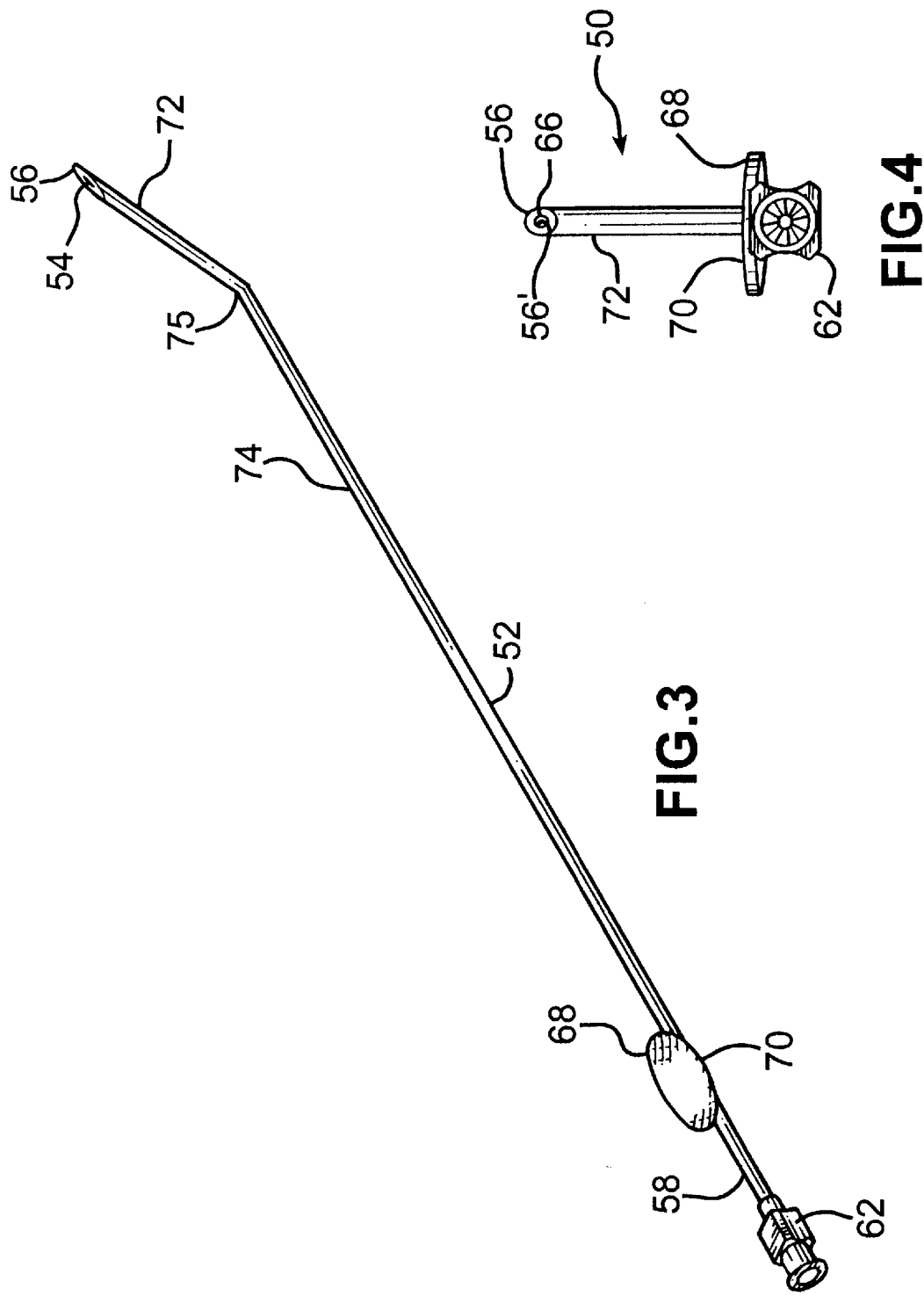

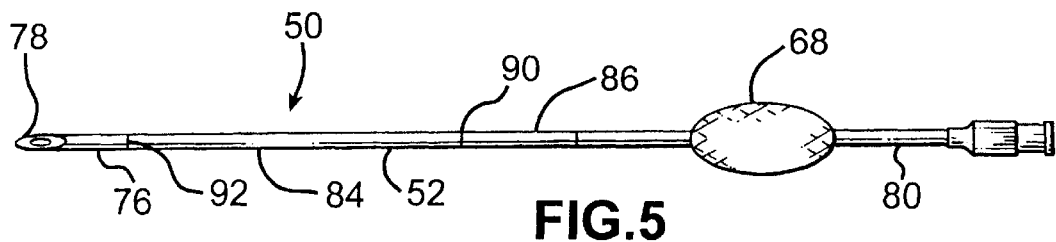
FIG. 5
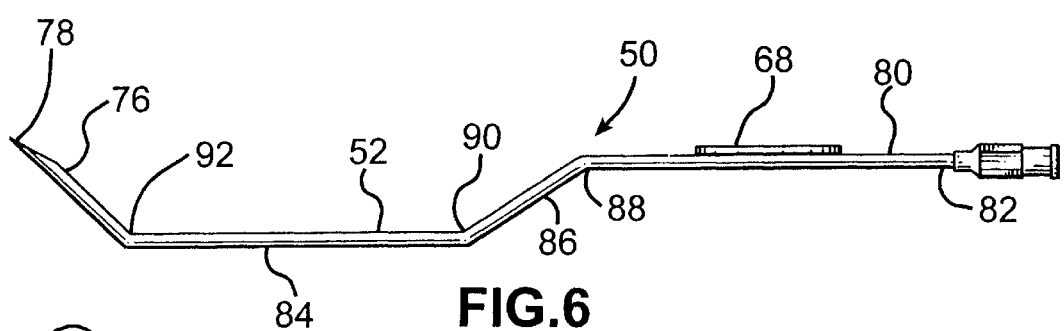
FIG. 6
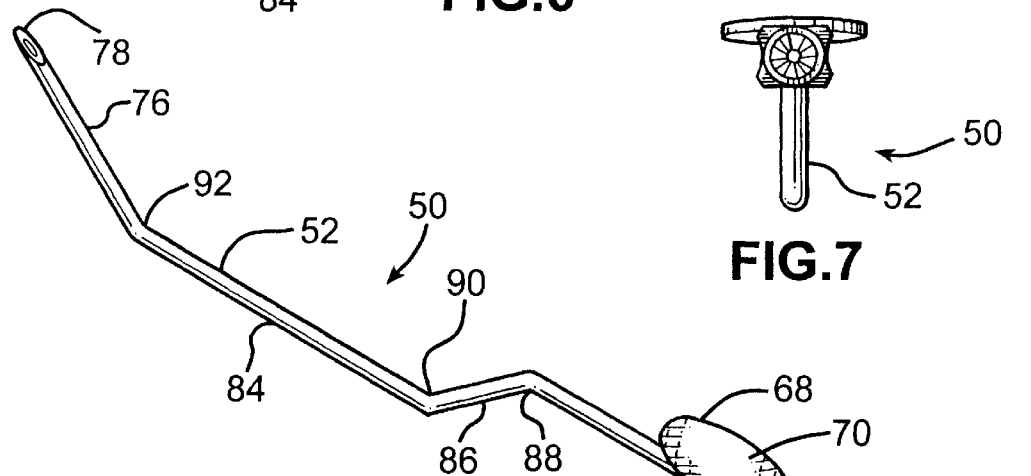
FIG. 7
FIG. 8
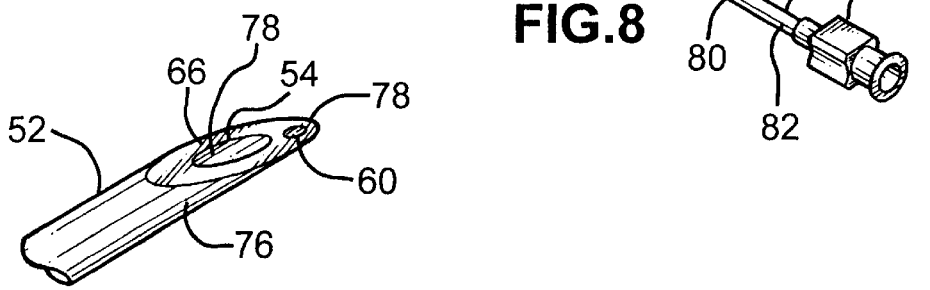
FIG. 8A

SUTURING NEEDLE ASSEMBLIES AND METHODS OF USE THEREOF

BACKGROUND OF THE INVENTION

This invention relates to suturing needle assemblies and methods of use thereof and more particularly to suturing needle assemblies for enabling simultaneous passage of suture and introduction of local anesthetic into body tissue. Methods of using the suturing needle assemblies include cystopexy, cystourethropexy, urethropexy and uteropexy procedures.

Stress urinary incontinence is a very common problem among females and is defined as involuntary loss of urine during coughing, laughing, sneezing or other physical activity. The most common cause of stress urinary incontinence among females is urethral hypermobility, significant displacement or prolapse of the urethra and bladder neck during strenuous physical activity, or the intrinsic urethral sphincter deficiency. Labor during childbirth, pelvic surgeries and menopause, among other conditions, lead to defects in the endopelvic fascia and the weakening of the support structures of the urethra and the bladder. During intrinsic sphincter deficiency the urethral sphincter is unable to generate enough resistance to retain urine in the bladder. This type of incontinence is commonly seen after vaginal surgeries, trauma, radiation, neurological disorders, aging or menopause. Patients with intrinsic sphincter deficiency may leak urine continuously or with minimal exertion.

Currently available methods of surgical treatment are expensive, invasive, require general anesthesia and are contraindicated in patients with other medical problems which put them into a higher surgical risk group. These methods (e.g. Kelly plication, Pereyra, Marshall-Marchetti-Krantz, Burch, Paravaginal repair) require incision that increases the risk of morbidity from the procedure. Patients with employment cannot afford to leave work for the time required for recovery from the conventional procedures, and these patients choose to suffer from urinary incontinence rather than being disabled temporarily. Commonly available procedures do not provide correction of urethral hypermobility or the intrinsic sphincter deficiency and simultaneous correction of the anatomical defects leading to cystocele and the drop in bladder neck.

Marshall-Marchetti-Krantz described a procedure where periurethral tissue is approximated to the symphysis pubis. This procedure involves abdominal incision and related complications including osteitis pubis. Burch described a procedure where the vaginal wall lateral to the bladder neck is elevated towards the cooper's ligament. This procedure also involves abdominal incision and related complications, including bladder damage with the suture material accidentally placed in the bladder as well as postoperative symptomatic enterocele and rectocele. The paravaginal repair involves reapproximating the endopelvic fascia to the pelvic wall at the arcus tendineus. This procedure also involves abdominal incision and related complications.

Pereyra described a technique where vaginal tissue on each side of the urethra is sutured to the fascia of the abdominal wall. This procedure also involves incision and related complications including injury to the surgeon's fingers with the risk of transmission of HIV, hepatitis and other infectious diseases.

Kelly plication involves dissection of vaginal wall and plication of pubocervical fascia. Procedures for intrinsic sphincter deficiency are sling procedures, artificial sphincter or the periurethral bulking injections. Sling procedures and artificial sphincter are more invasive procedures requiring extensive use of synthetic materials. Periurethral injections are expensive and provide only temporary relief.

Against this background, a need exists for surgical devices and procedures offering the least invasive, safe and effective alternative to existing methods for the surgical treatment of urinary incontinence.

It is, therefore, an object of the present invention to provide surgical tools and methods for overcoming the problems and limitations of the prior art.

Another object of the present invention is to provide suturing needle assemblies and surgical procedures for enabling simultaneous passage of suture and introduction of local anesthetic into body tissue.

Another object is to provide such needle assemblies and procedures which are used for surgical management of female urinary incontinence and other pelvic floor disorders under local anesthesia without the need for use of general anesthesia.

A further object of the invention is the provision of such needle assemblies and procedures for use in the surgical management of female urinary incontinence and other pelvic floor disorders without requiring an incision in the patient.

Still another object is to provide such needle assemblies and procedures which reduce the risk of complications, such as bleeding and infections.

Yet another object of the present invention is the provision such needle assemblies and procedures which enable patients to go home more promptly after surgery.

Another object is to provide such needle assemblies and procedures which permit the surgeon to safely perform the procedures of this invention on patients in whom traditional procedures are contraindicated due to other medical conditions.

A further object of the invention is the provision of such needle assemblies and procedures which reduce the cost of traditional surgical procedures for management of female urinary incontinence and other pelvic floor disorders.

Another object is to provide needle assemblies and procedures and procedures for use of the needle assemblies which enable the procedures to be performed in a physician's office, outpatient surgery center or mobile medical unit so as to provide patients from rural areas access to modern medical care.

Another object is to provide needle assemblies and procedures for surgical management of female urinary incontinence and other pelvic floor disorders which reduce the chance of injury or transmission of infectious disease to the surgeon.

A further object of the invention is the provision of needle assemblies and methods of using the needle assemblies for surgical management of female urinary incontinence and other pelvic floor disorders which reduces the cost of surgery by eliminating the cost of inpatient care after surgery and by eliminating the cost for general anesthesia.

Another object is to provide such needle assemblies and procedures which reduce the possibility of accidental damage to organs of the patient during the surgical procedures.

Another object is to provide instruments and surgical techniques which allow for permanent correction of the anatomical defects leading to pelvic organ prolapse and urinary incontinence.

A further object is to provide instruments and surgical techniques that are minimally invasive and which provide a bigger, stronger area of anchoring on the abdominal muscles.

Still another object is to provide instruments and surgical techniques which decrease the chances of sutures cutting through.

Another object is to provide instruments and surgical techniques where there is no synthetic support material under the bladder or on the abdomen.

A further object is to provide instruments and surgical techniques for their use wherein the techniques are easy to perform, reproducible and safe for the surgeon and the patient.

Additional objects and advantages of the invention will be set forth in part in the description which follows, and in part will be obvious from the description, or may be learned by practice of the invention. The objects and advantages are realized and attained by means of the instrumentalities and combinations particularly pointed out in the appended claims.

SUMMARY OF THE INVENTION

To achieve these and other objects, the present invention provides a suturing needle assembly for enabling simultaneous passage of suture and introduction of local anesthetic into body tissue, the assembly comprising: a hollow needle body defining an interior passageway and further defining first and second ends having first and second openings therein, respectively, in fluid communication with the passageway; the first end further defining a third opening therein for removably receiving a suture; and means connected to the second end for removably attaching the needle assembly to a source of local anesthetic.

It is to be understood that both the foregoing general description and the following detailed description are exemplary and explanatory but are not restrictive of the invention.

BRIEF DESCRIPTION OF THE DRAWINGS

The accompanying drawings, which are incorporated in and constitute a part of this specification, illustrate preferred embodiments of the invention and, together with the description, serve to explain the principles of the invention.

FIG. 3 is a perspective view of the needle assembly shown in FIG. 1;

FIG. 4 is an end elevation view of the needle assembly shown in FIG. 1;

FIG. 5 is a top plan view of a second needle assembly embodiment in accordance with the invention;

FIG. 6 is a side elevation view of the needle assembly shown in FIG. 5;

FIG. 7 is an end elevation view of the needle assembly shown in FIG. 5;

FIG. 8 is a perspective view of the needle assembly shown in FIG. 5;

FIG. 8A is a fragmentary perspective view of an end portion of the needle assembly shown in FIG. 5;

DESCRIPTION OF THE PREFERRED EMBODIMENT

Figure 1A:
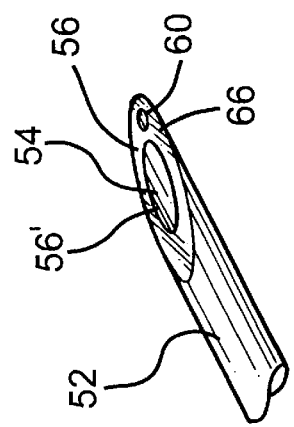
FIG. 1A is a fragmentary perspective view of an end portion of the needle assembly shown in FIG. 1.
Figure 1:
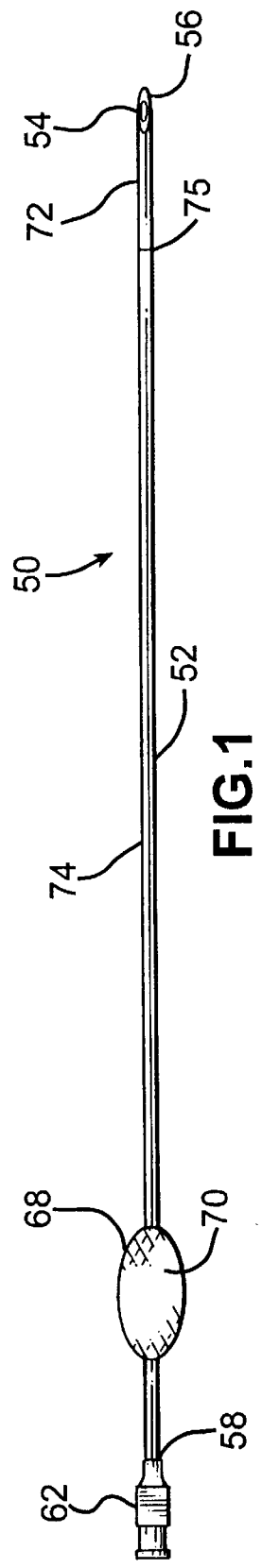
FIG. 1 is a top plan view showing a first embodiment of a needle assembly in accordance with the invention.
Figure 2:
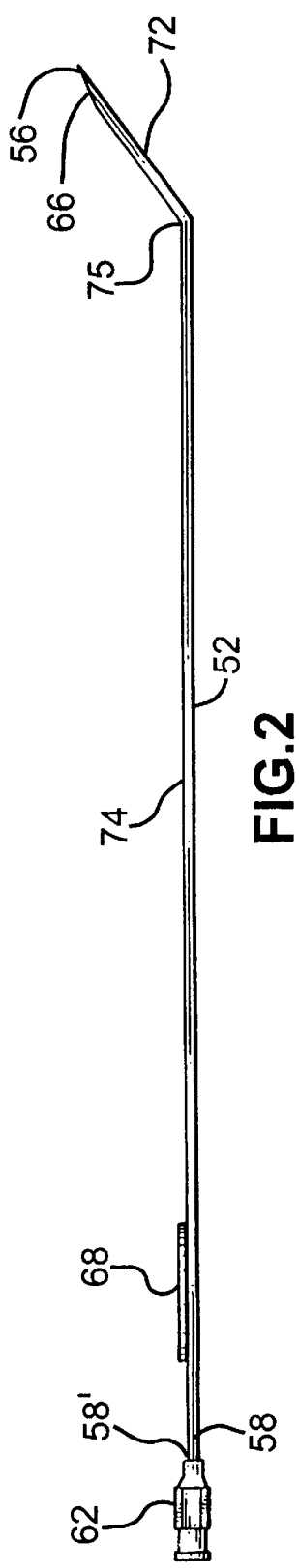
FIG. 2 is a side elevation view of the needle assembly shown in FIG. 1.

With reference now to the drawings, wherein like reference characters designate like or corresponding parts throughout the several views, there is shown in FIGS. 1–4 a first suturing needle assembly embodiment 50 for enabling simultaneous passage of suture and introduction of local anesthetic into body tissue. In accordance with the invention, assembly 50 comprises a hollow, elongated needle body 52 defining an interior passageway 54 which extends the full length of needle body 52, and further defining first and second ends 56, 58 having first and second openings 56', 58', respectively, therein in fluid communication with passageway 54.

Figure 10:
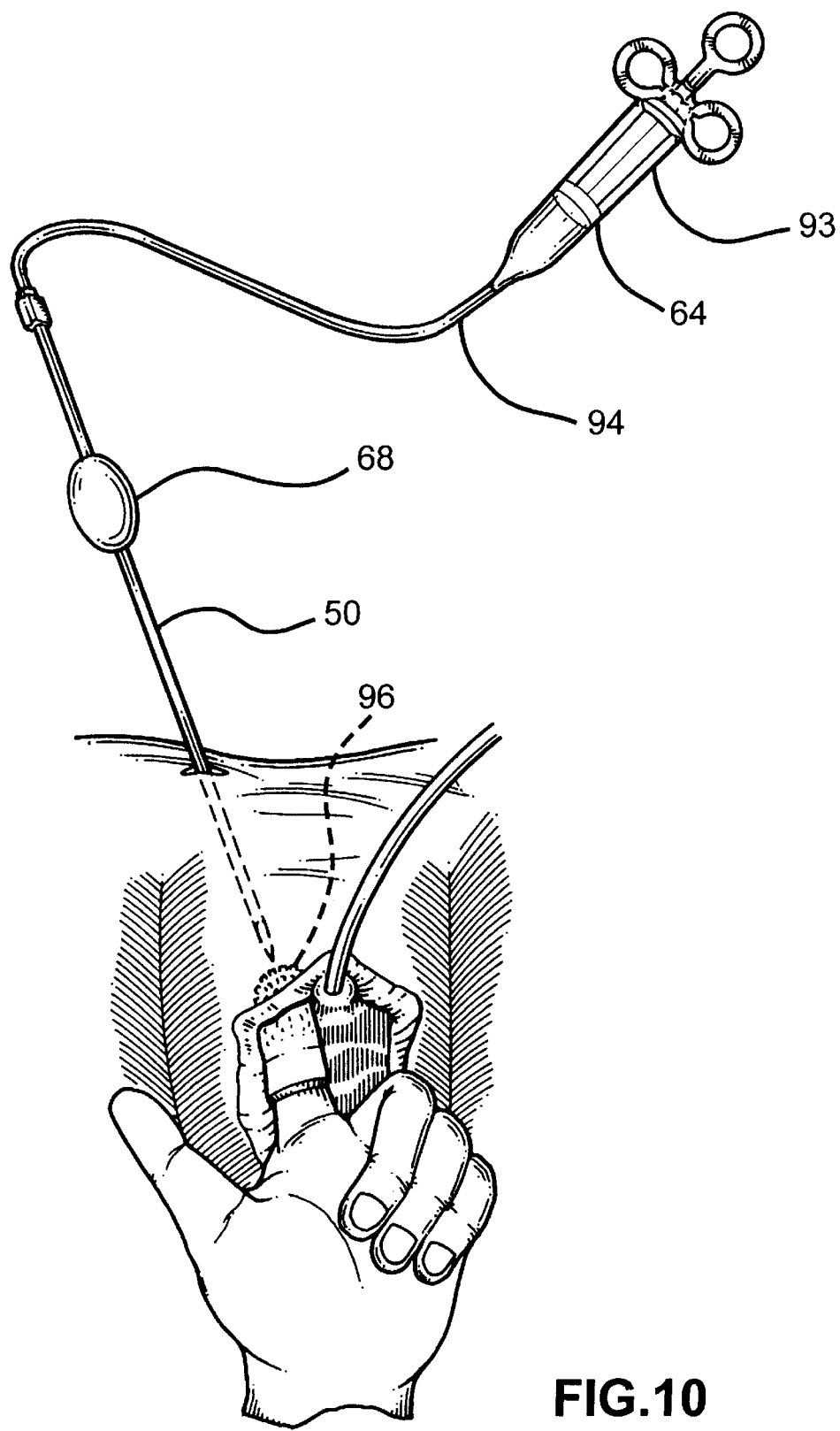

First end 56 further defines a third opening 60 therein for removably receiving a suture, and means 62 are connected to second end 58 for removably attaching needle assembly 50 to a source of local anesthetic 64 (see FIG. 10) in a conventional manner.

In accordance with the invention, first end 56 is a slightly blunted sharp end for decreasing the risk of accidental injuries and is beveled with respect to needle body 52 to form a beveled end surface 66 (see FIG. 1A). Third opening 60 extends through beveled end surface 66 for enabling a suture to removably pass through opening 60.

Means 68 are attached to needle body 52 in a conventional manner, such as by welding, for enhancing a user's grip of needle assembly 50 during use thereof. Surface 70 of gripping means 68 is preferably roughened or scored to provide enhanced gripping of gripping means 68 by a user and to provide enhanced control of needle assembly 50 during surgical procedures.

Needle body 52 defines a first straight portion 72 adjacent to first end 56 and a second straight portion 74 connected to first straight portion 72 and adjacent to second end 58. First and second straight portions 72, 74 define an angle 75 therebetween of from one hundred ten degrees to one hundred eighty degrees, but preferably one hundred forty-five degrees. Needle assembly 50 is preferably made from stainless steel.

A second needle assembly embodiment 50' is shown in FIGS. 5–8A. Needle assembly 50' comprises a hollow, elongated needle body 52' which defines a first straight portion 76 adjacent to first end 78. Needle body 52' further defines a second straight portion 80 adjacent to second end 82. Needle body 52' further defines a third straight portion 84 connected to first straight portion 76 and a fourth straight portion 86 connected between portions 80 and 84. Fourth portion 86 defines first and second angles 88, 90 with each of straight portions 80, 84, respectively. Angles 88, 90 are from one hundred fifteen degrees to one hundred seventy-five degrees but preferably one hundred forty-five degrees, and angles 88, 90 are equal to each other.

First and third straight portions 76, 84 define a third angle 92 therebetween of from one hundred five degrees to one hundred sixty-five degrees but preferably one hundred thirty-five degrees.

Needle assembly 50' is preferably configured wherein second straight portion 80 defines an extended imaginary straight center line therethrough (not shown) which intersects with first straight portion 76. This configuration is best seen in FIG. 6.

Needle assembly 50' defines an interior passageway 54' which extends the entire length of assembly 50' between ends 78 and 82. First end 78 is a slightly blunted sharp end for decreasing accidental injuries and is beveled with respect to straight portion 76 of needle body 52' to form a beveled end surface 66' (see FIG. 8A). Opening 60' extends through beveled end surface 66' for enabling a suture to removably pass through opening 60'.

Means 68' are attached to portion 80 of needle assembly 50' in a conventional manner, such as by welding, for enhancing a user's grip of needle assembly 50' during use thereof. Surface 70' of gripping means 68' is preferably roughened or scored to provide enhanced gripping of gripping means 68' by a user and to provide enhanced control of needle assembly 50' during surgical procedures.

Figure 16:
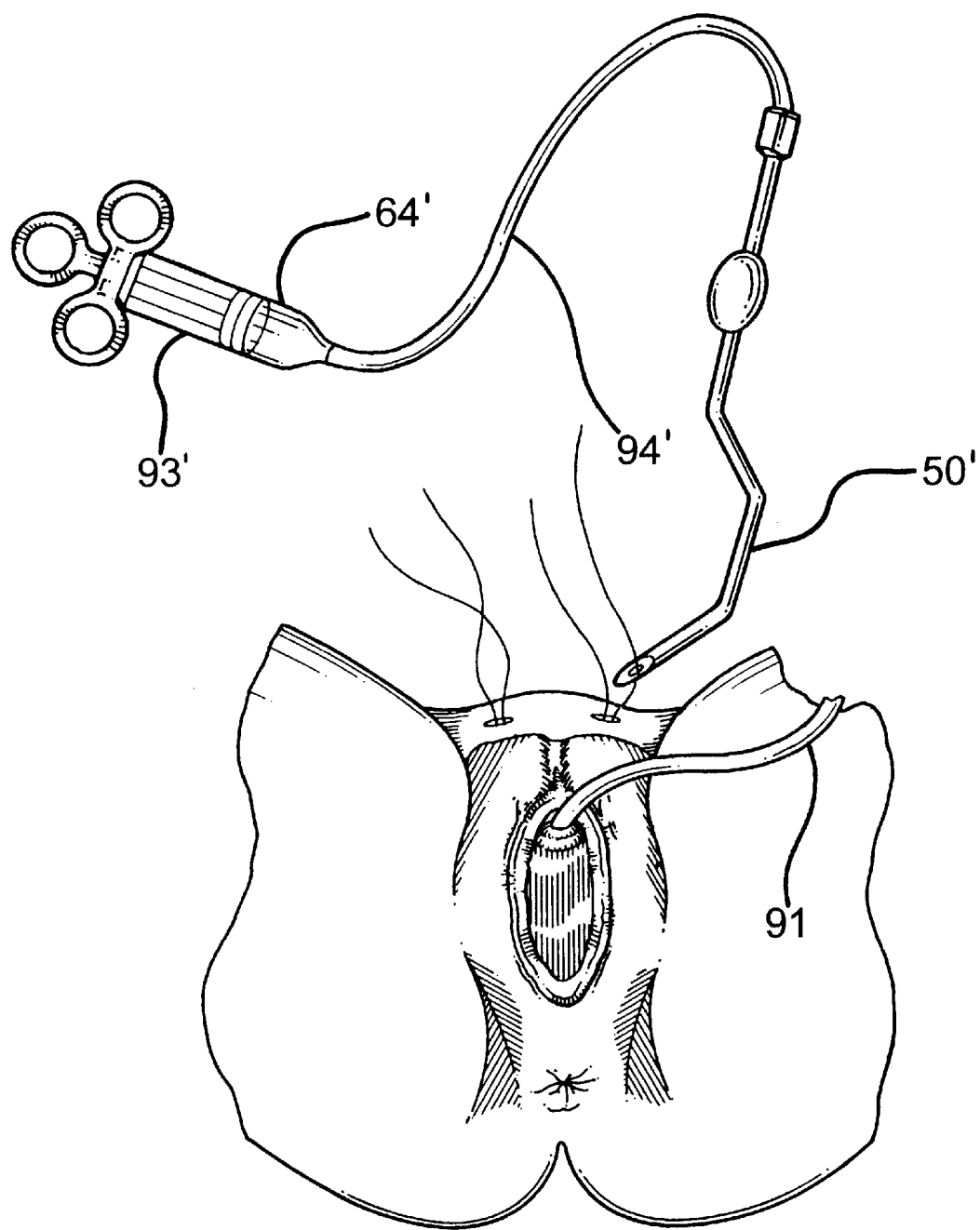

Means 62' are conventionally connected to second end 82 for removably attaching needle assembly 50' to a source of local anesthetic 64' (see FIG. 16) in a conventional manner. Needle assembly 50' is preferably made from stainless steel.

Needle assembly 50 is configured for allowing simultaneous infiltration of local anesthetic and the passage of suture from the patient's bladder neck and paraurethral area in the vaginal wall to the anterior abdominal wall for urinary incontinence or other pelvic floor relaxation surgeries. Needle assembly 50' is configured for allowing simultaneous infiltration of local anesthetic and the passage of suture from one side of the patient's anterior abdominal wall to the other side for urinary incontinence and other pelvic floor relaxation surgeries. Needle assembly 50' allows passage of suture under the skin, therefore eliminating the need for an incision.

It should be understood, however, that this invention also contemplates needles of different configurations for enabling the simultaneous passage of suture and the introduction of local anestheic through the hollow needle into body tissue.

The configuration of needle assembly 50 protects organs of the patient from being damaged by needle assembly 50 because blunted sharp end 56 points toward the patient's pubic bone during the surgical procedures. The chances of accidentally damaging other organs of the patient during the surgical procedures are almost eliminated and allows the surgeon to comfortably drive needle assembly 50 behind the patient's pubic bone.

The configuration of needle assembly 50' also protects organs of the patient from being damaged by needle assembly 50' during the surgical procedures because blunted sharp end 78 of needle assembly 50' points toward the patient's skin during the procedures. The configuration of needle assembly 50' also gives the surgeon peace of mind because the chances of accidentally damaging other organs of the patient are eliminated and allows the surgeon to comfortably drive the needle of assembly 50' underneath the patient's skin. The configuration of needle assembly 50', angle 92 and the relative length of straight portion 76 allows comfortable passage of suture.

Use of needle assemblies 50 and 50' generally comprises the steps of positioning a conventional suture into and through openings 60, 60' of needle assemblies 50, 50', respectively, and attaching a source 64, 64' of local anesthetic to needle assemblies 50, 50' in a conventional manner to attaching means 62, 62' of needle assemblies 50, 50', respectively.

Blunted sharp ends 56, 78 of needle assemblies 50, 50', respectively, are introduced with the attached sutures into body tissue while local anesthetic is simultaneously passed from sources 64, 64' through hollow interior passageways 54, 54' of assemblies 50, 50', respectively.

The local anesthetic is introduced into the body tissue by passing the local anesthetic from sources 64, 64' through openings 58', 82', respectively, of assemblies 50, 50' and through interior passageways 54, 54' of assemblies 50, 50', respectively, and through openings 56', 78', of assemblies 50, 50', respectively, into the body tissue. Specific surgical procedures are provided in accordance with this invention which use needle assemblies 50, and 50'. The specific surgical procedures will now be described in detail.

Cystopexy

1. Prep and drape the patient in usual fashion in low lithotomy position. Drain the bladder.

2. Place a dot with marking pen 4 cm lateral from the midline on both sides just above the edge of the pubis.

3. Apply 1% Xylocaine jelly in the urethra and bladder.

4. Place a 4 inch×4 inch gauze pad soaked with 1% Xylocaine jelly in anterior portion of the vagina and remove after a few minutes.

5. Insert a weighted speculum to depress the posterior vagina.

6. Insert a 20 French Foley catheter 91 with 30 cc balloon, inflate and clamp.

7. Inject 1 cc of 1% Xylocaine into the skin at pen marks on both sides above the pubis.

8. Inject 1 cc of 1% Xylocaine on both sides 1 cm lateral at the level of the bladder neck.

Figure 9:
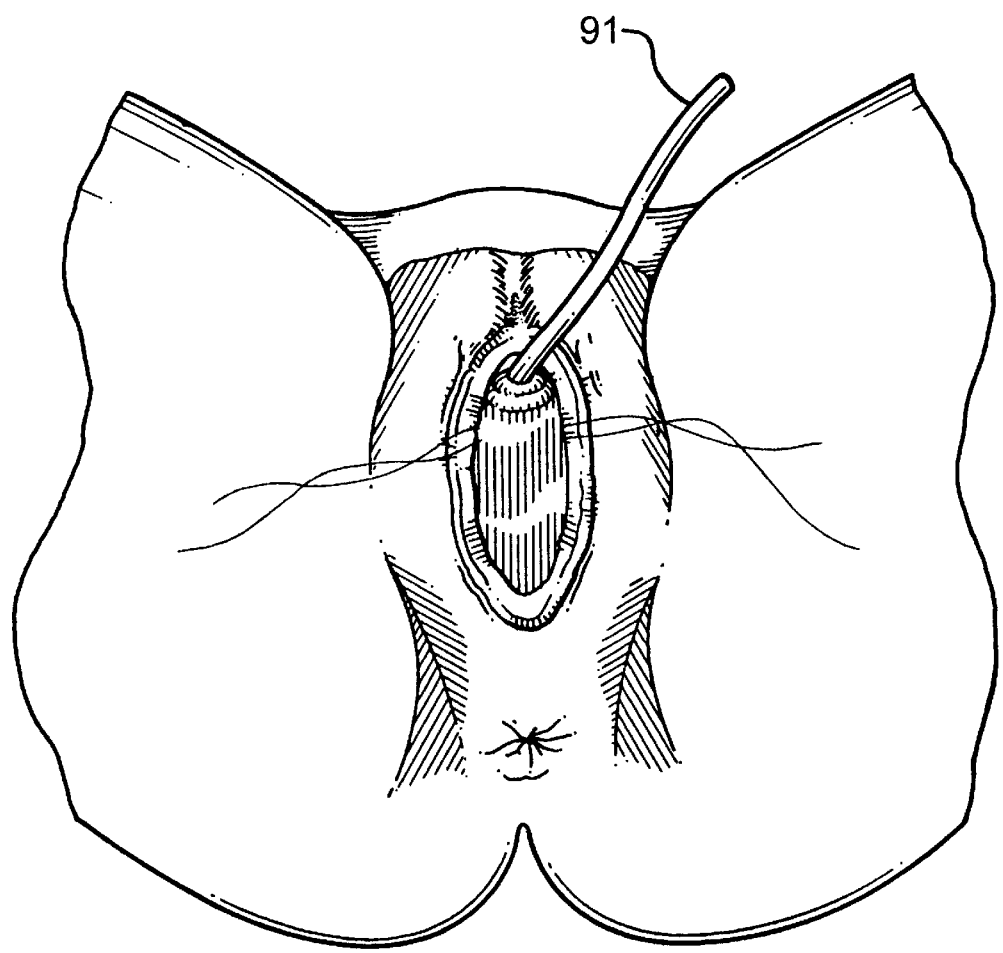
FIGS. 9–19 show use of the needle assemblies illustrated in FIGS. 1 and 5 in cystopexy, uteropexy and urethropexy surgical procedures.

9. Place a 3 loop suture 1 cm lateral at the level of the bladder neck on both sides using a #1 Novafil on CT1 needle (or similar permanent suture) through the entire thickness of the vagina. Do not tie the knot. Hold the suture with straight Kelly clamps. (See FIG. 9.)

10. Fill a 15 cc syringe 93 with 1% Xylocaine. Attach syringe 93 to needle assembly 50 with small IV extension tubing 94 in a conventional manner.

11. Drain needle 50 to remove the air.

12. Thumbpiece 68 on needle 50 is firmly grasped, angled and directed towards the posterior pubis at the right pen mark. Needle 50 is introduced into the retropubic space paravesically along the posterior aspect of the pubic bone. (See FIG. 10.) Assistant continuously injects Xylocaine while needle 50 is driven. Assistant as well pulls the Foley catheter to the contralateral side.

Figure 11:
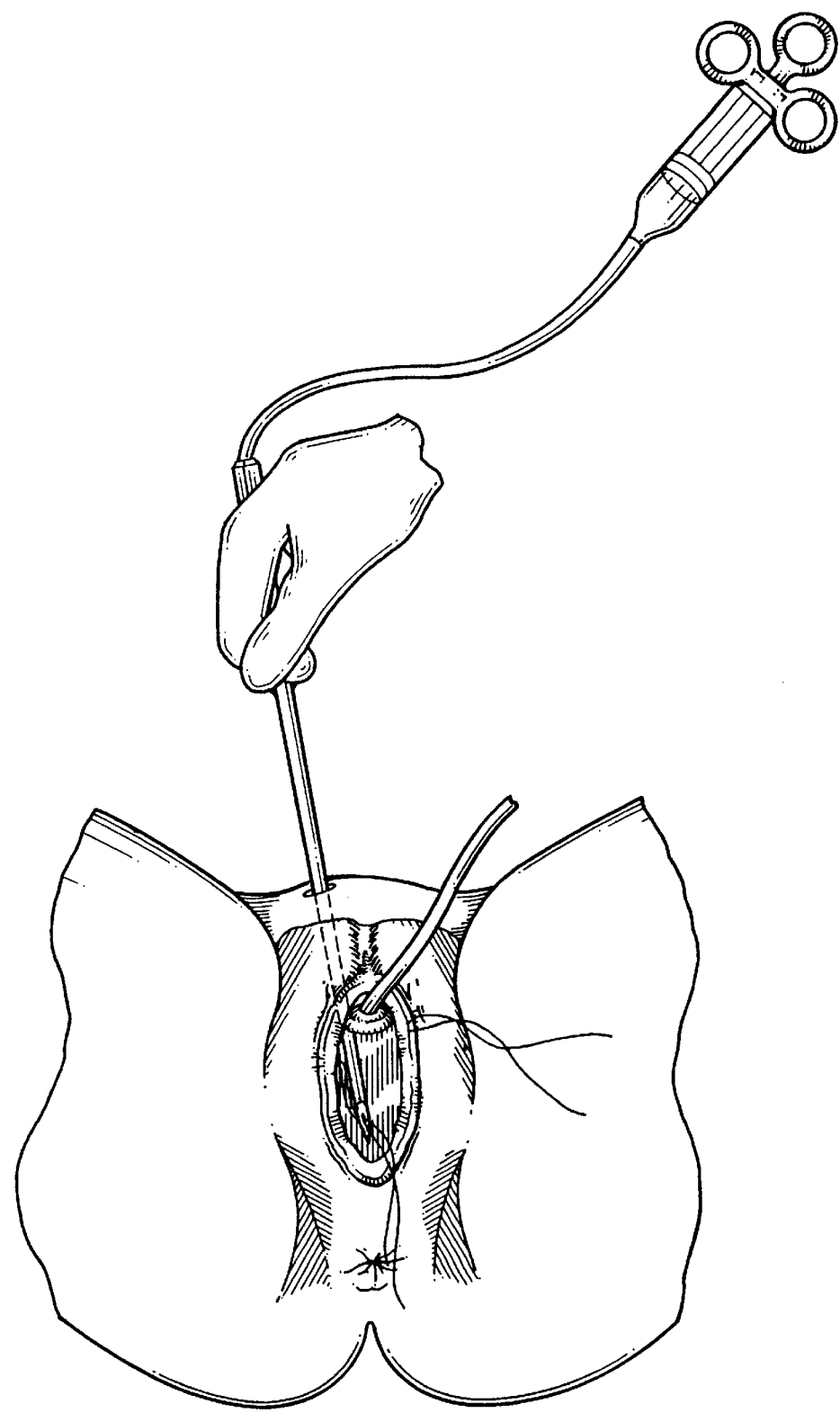
Figure 12:
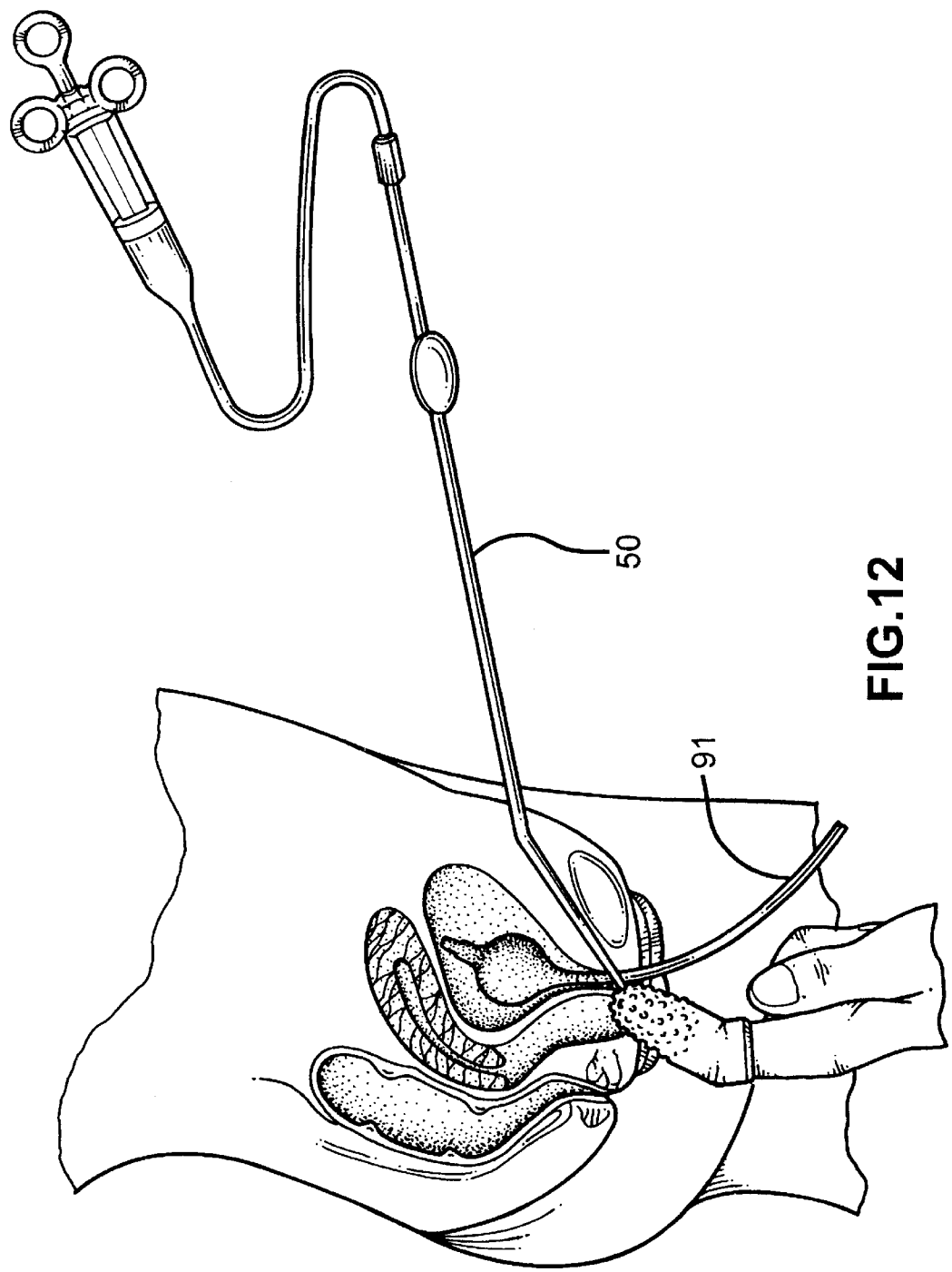

13. Index finger with a thimble 96 is placed in the right side of vagina lateral to the bladder neck and pushed upwardly behind the pubis. Needle 50 is guided over thimble 96 until it emerges through the vagina. (See FIGS. 10–12.)

14. Disconnect needle 50 from tubing 94.

15. Steps 10 through 14 are repeated on the contralateral side.

16. Catheter 91 is removed and cystoscopy is performed with a 70-degree lens to rule out bladder perforation.

17. Foley catheter 91 is placed as in step 6.

Figure 13:
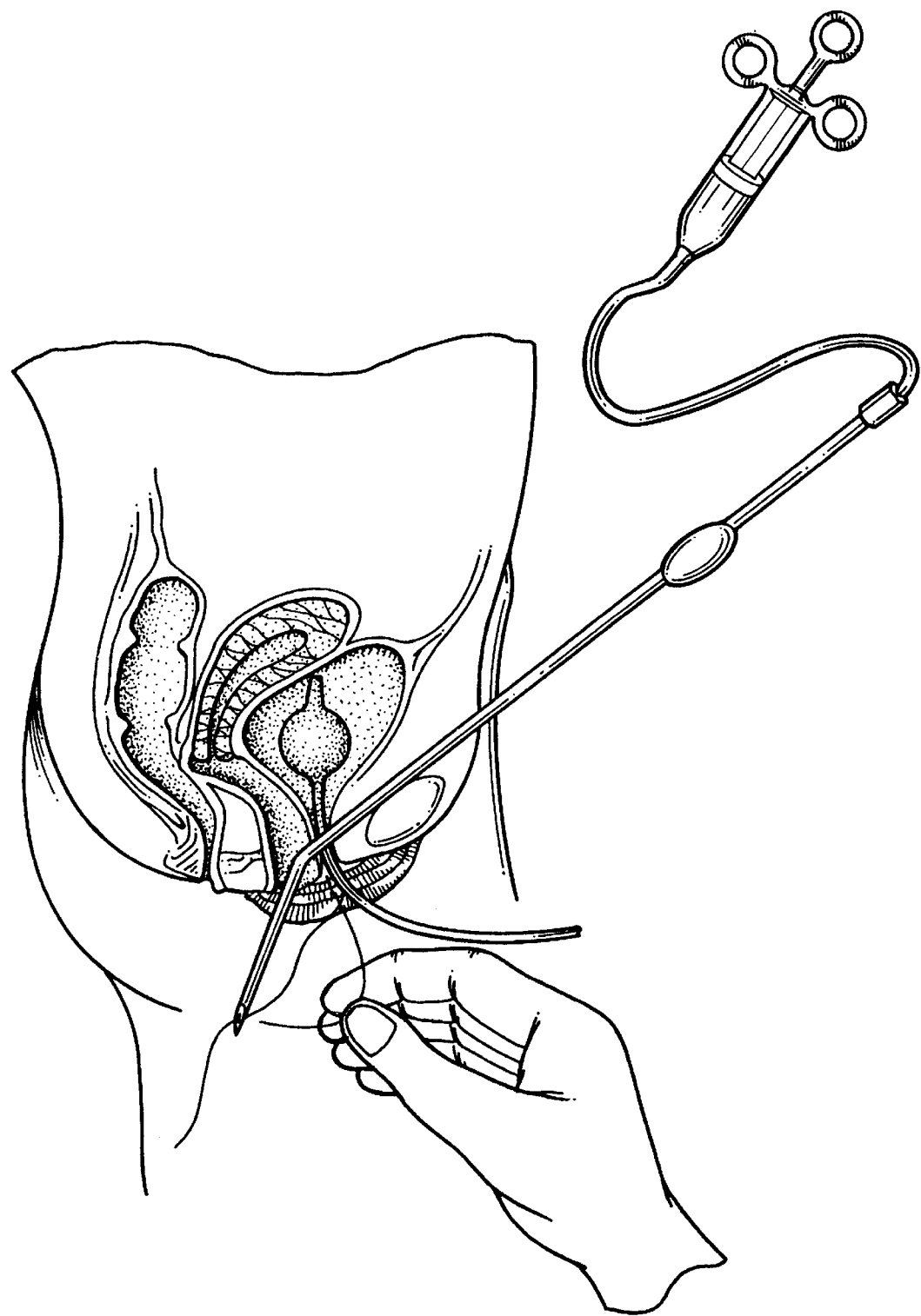

18. Suture from the straight Kelly clamps is passed through hole 60 in needle 50 on both sides of the patient. (See FIG. 13.)

Figure 14:
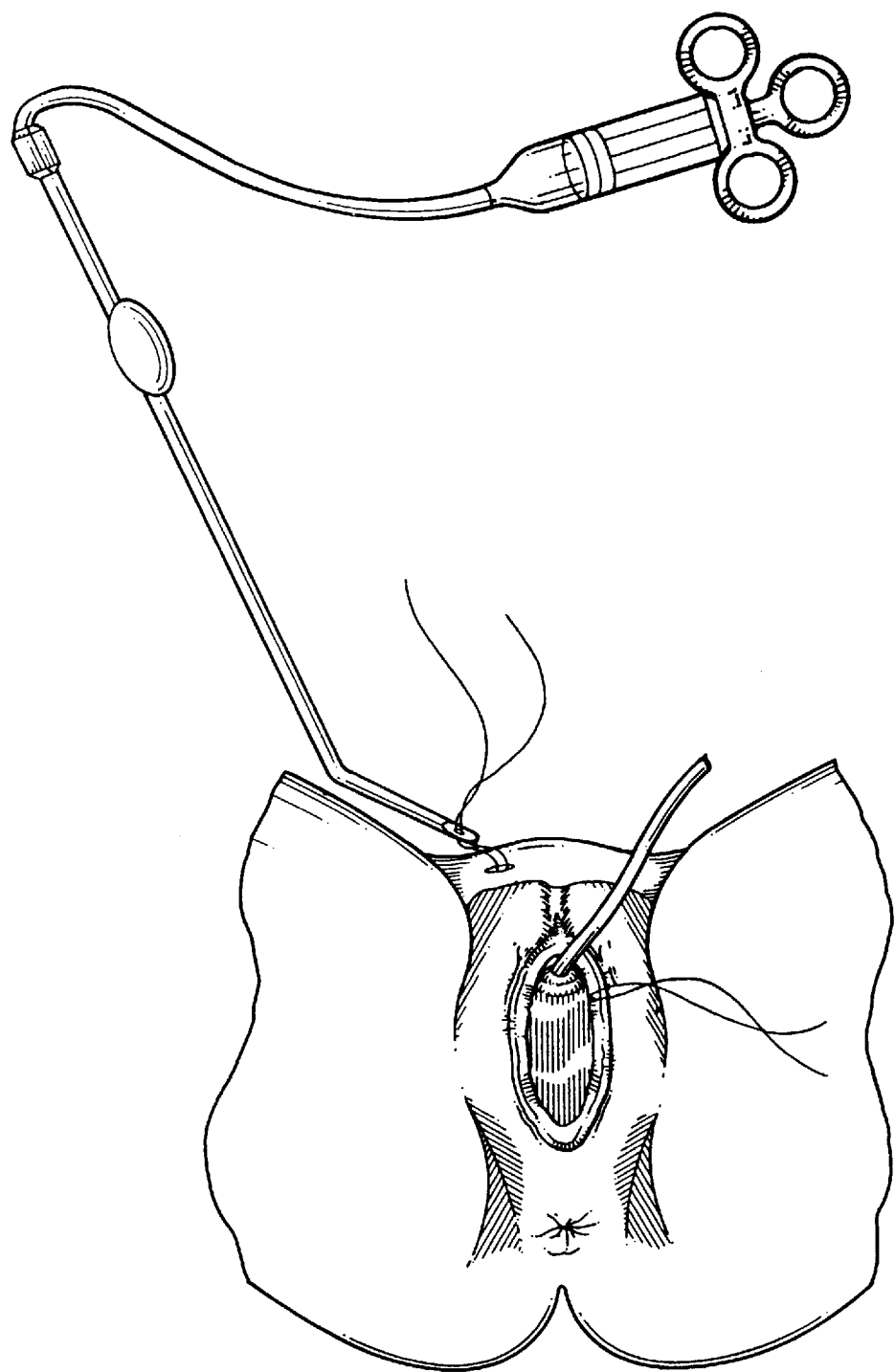
Figure 15:
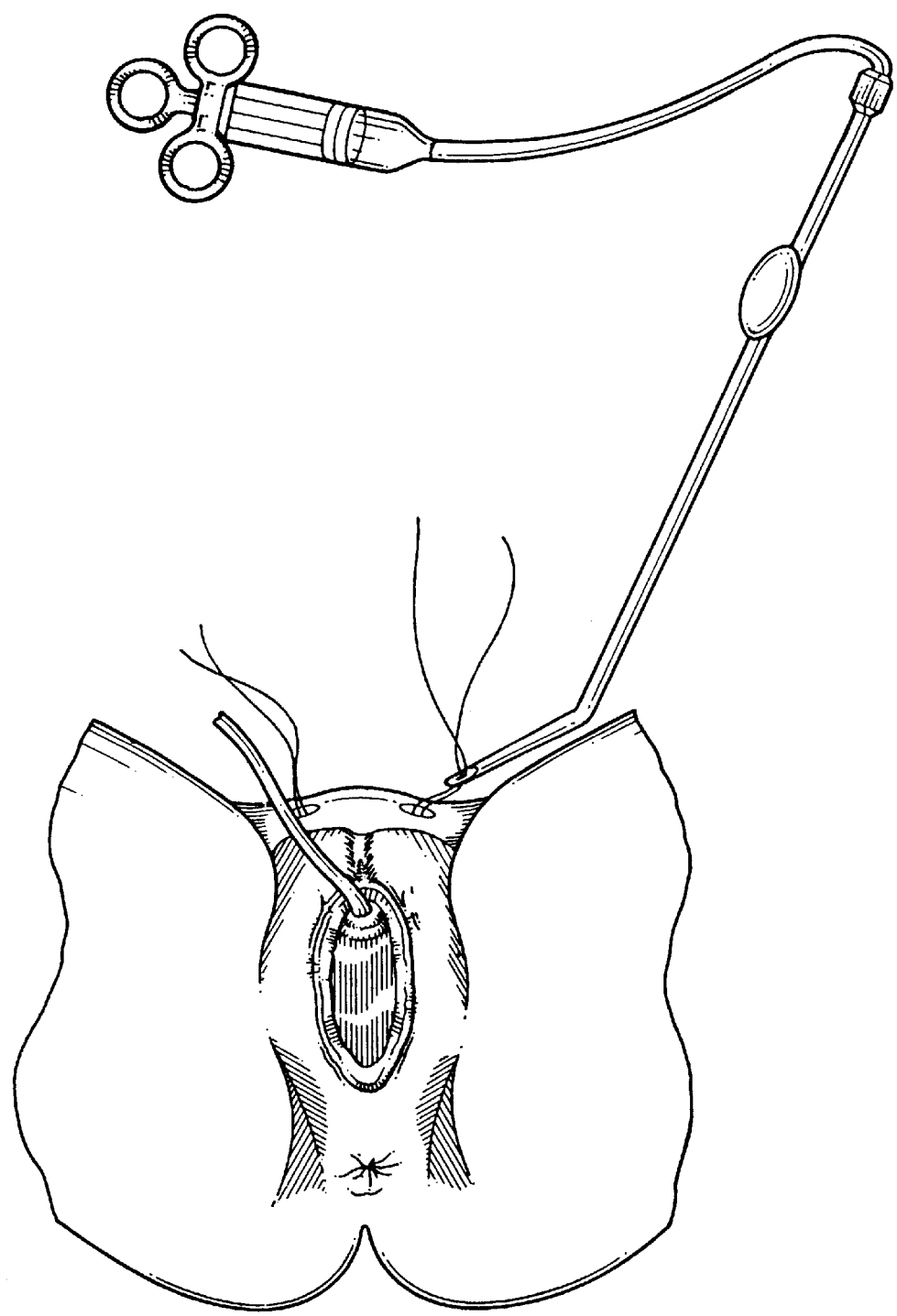

19. Needles 50 are pulled back slowly along the posterior aspect of the pubis until sutures are pulled through the anterior abdominal wall. (See FIGS. 14 and 15.)

20. Needle 50 is removed and suture grasped with straight Kelly clamp on both sides.

21. Steps 10 and 11 are repeated with needle assembly 50'.

22. Release one arm of the left suture and thread through hole 60' in needle 50'. (See FIG. 16.) Hold the other suture arm with a straight Kelly clamp.

Figure 17:
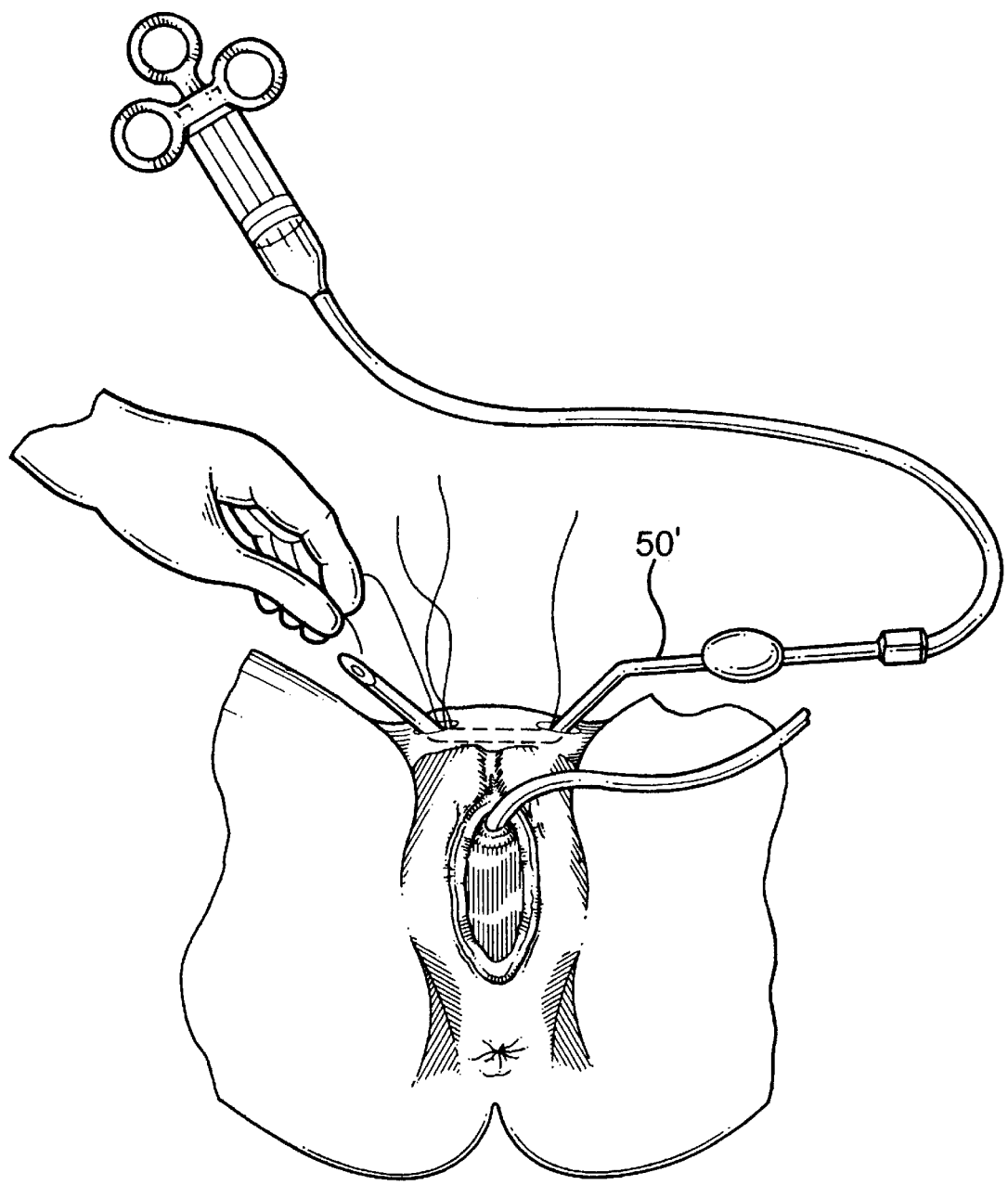

23. Introduce needle 50' into the left skin puncture site. Continuously injecting Xylocaine drive needle 50' pointing downwardly then laterally just above the fascia and finally upwardly until it emerges through the right skin puncture site. (See FIG. 17.)

24. Release the suture from needle 50'.

25. Release one arm of the right suture and thread through hole 60' in needle 50'. (See FIG. 17.) Hold the other suture arm with the straight Kelly clamp along with the remaining left suture arm.

26. Pull needle 50' back until suture emerges through the left puncture site. Release the right suture from needle 50' and hold the right suture with left straight Kelly clamp.

27. Release Kelly clamps, apply slight traction on the sutures on both sides and reapply the Kelly clamps.

28. Assistant elevates the patient's bladder neck by pushing the anterior vaginal wall upwardly behind the pubis with fingers.

Figure 18:
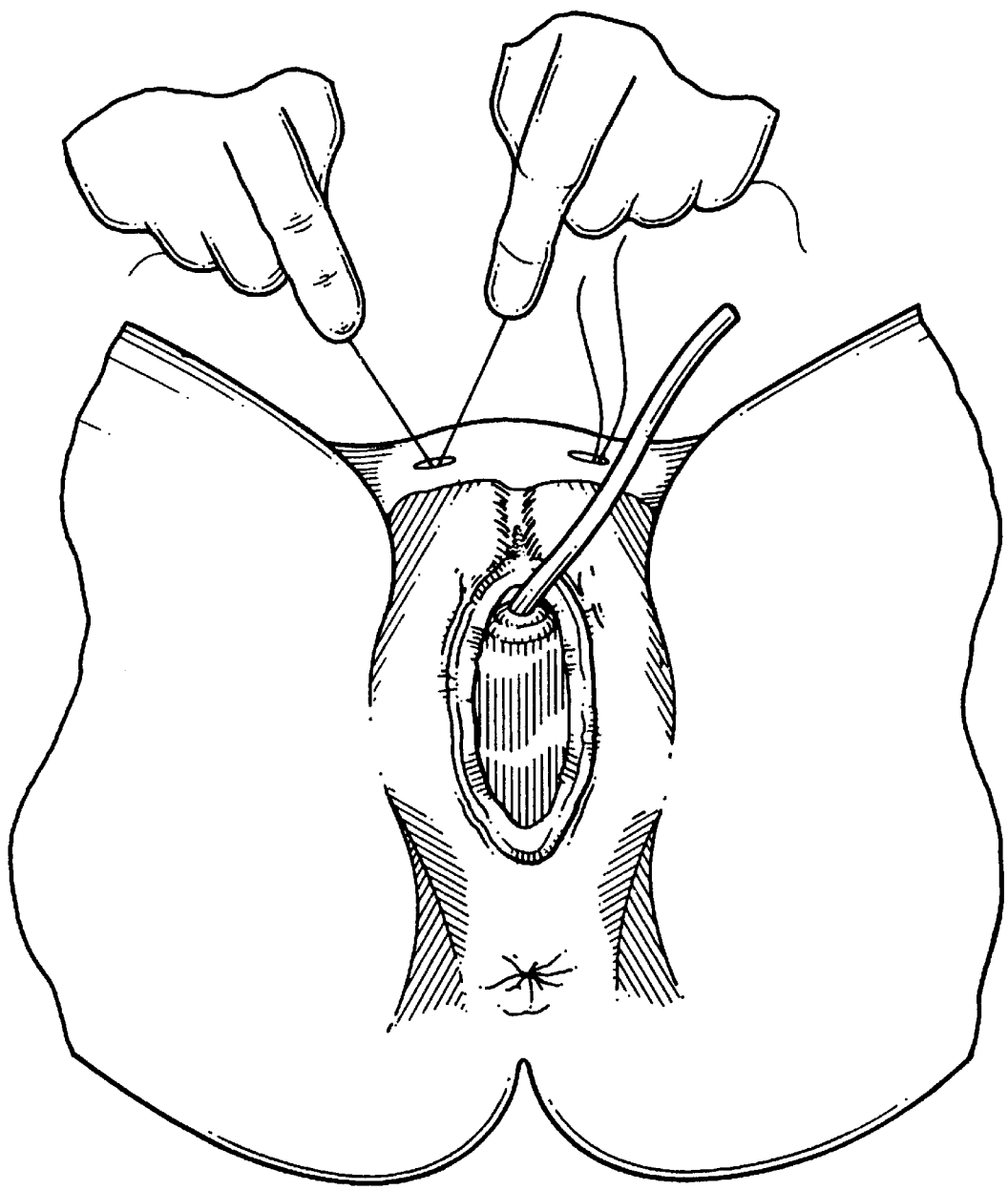
Figure 19:
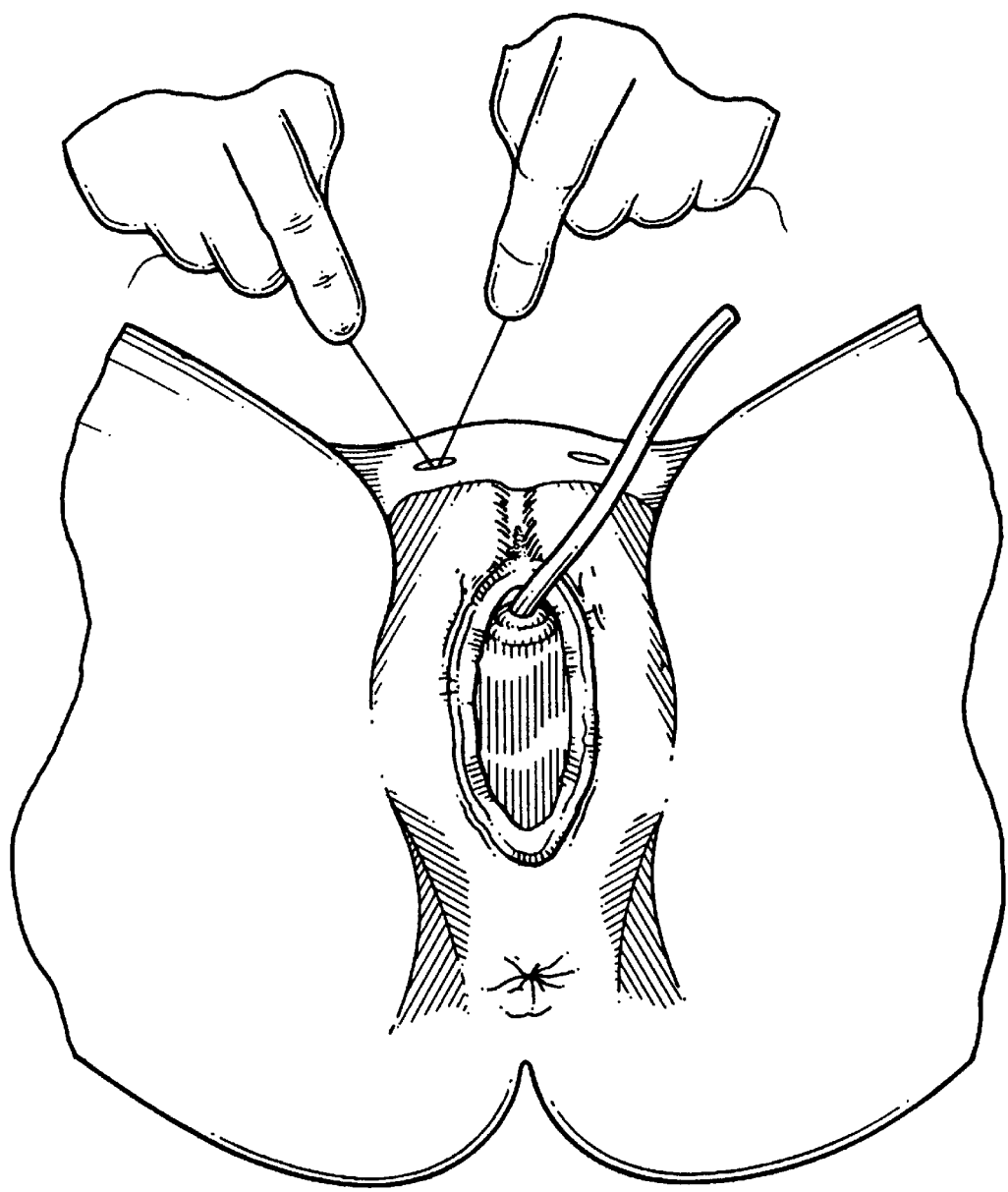

29. When the bladder neck is in normal anatomical position, elevated by assistant's fingers, tie the sutures on both sides with 8 knots into the skin puncture sites (see FIGS. 18 and 19) and cut the sutures right above the knots.

30. Lift the edges of the puncture sites bilaterally with Edson forceps and allow the knots to retract.

31. Apply sterile strips on puncture sites.

32. Clamp on the Foley catheter 91 is now removed. Patient is transferred to the recovery area with urinary drainage bag. Foley catheter 91 is removed before transfer if patient is prescribed intermittent self-catheterization.

Cystourethropexy

1. Prep and drape the patient in usual fashion in low lithotomy position. Drain the bladder.

2. Place a dot with marking pen 4 cm lateral from the midline on both sides just above the edge of the pubis.

3. Apply 1% Xylocaine jelly in the urethra and bladder.

4. Place a 4 inch×4 inch gauze pad soaked with 1% Xylocaine jelly in anterior portion of the vagina and remove after a few minutes.

5. Insert a weighted speculum to depress the posterior vagina.

6. Insert a 20 French Foley catheter 91 with 30 cc balloon, inflate and clamp.

7. Inject 1 cc of 1% Xylocaine into the patient's skin at pen marks on both sides above the pubis.

8. Inject 1 cc of 1% Xylocaine on both sides 1 cm lateral at the level of the bladder neck.

Figure 20:
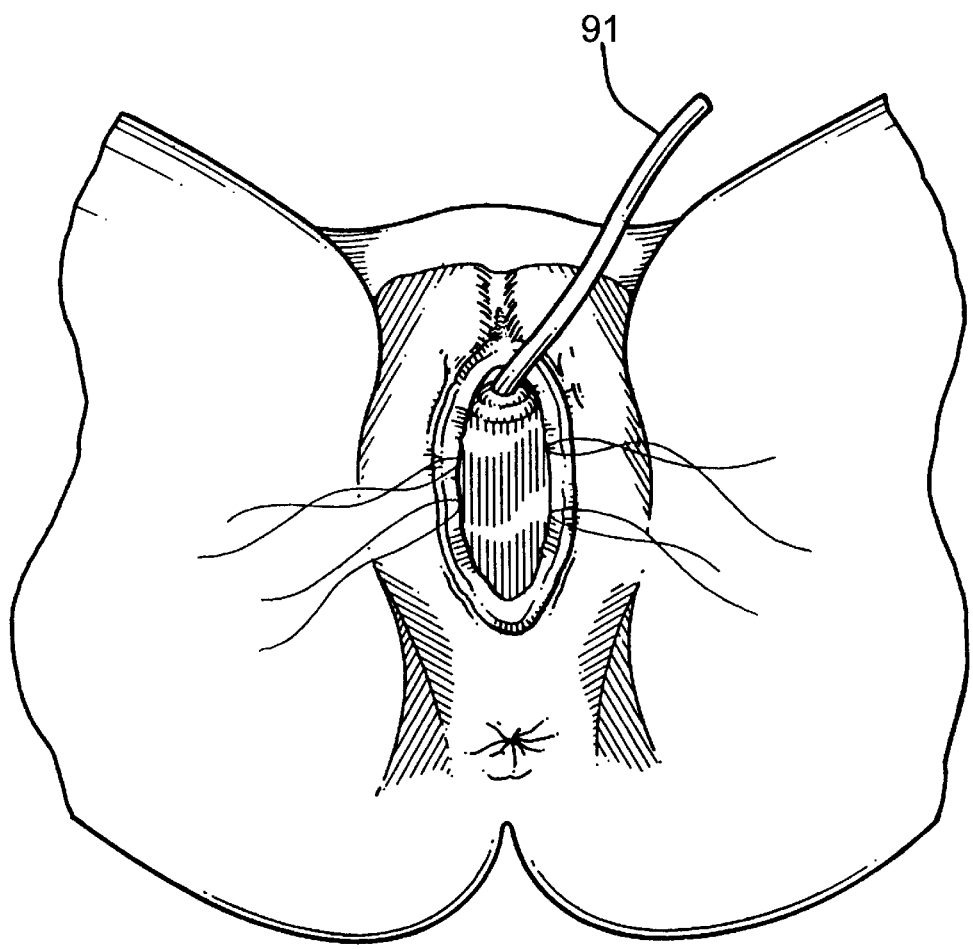
FIGS. 20–28 show use of the needle assemblies illustrated in FIGS. 1 and 5 in a cystouretheropexy surgical procedure.

9. Place a 3 loop suture 1 cm lateral at the level of the bladder neck on both sides using a #1 Novafil on CT1 needle (or similar permanent suture) through the entire thickness of the vagina. Do not tie the knot. Hold the suture with straight Kelly clamps. (See FIG. 20.)

10. Place a 3 loop suture 1 cm lateral at the level of proximal ⅓ of the urethra on both sides using #1 Novafil on CT1 needle (or similar permanent suture) through the entire thickness of the vagina. Do not tie the knot. Crush the ends with the needle holder for later identification. Hold the suture with curved Kelly clamps. (See FIG. 20.)

11. Fill a 15 cc syringe 93 with 1% Xylocaine. Attach the syringe to needle 50 with small IV extension tubing 94 in a conventional manner.

12. Drain needle 50 to remove the air.

Figure 21:
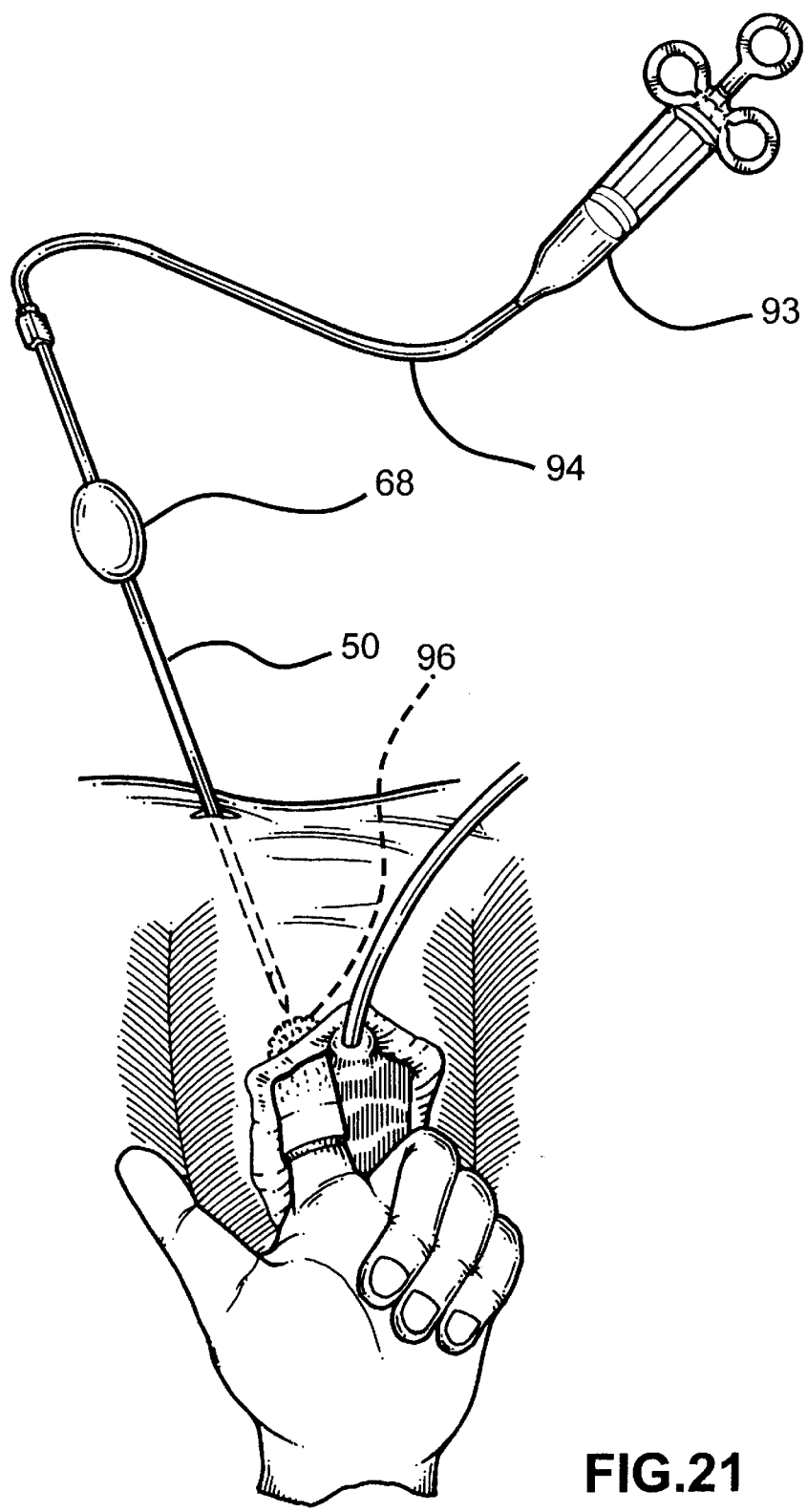

13. Thumbpiece 68 on needle 50 is firmly grasped, angled and directed towards the posterior pubis at the right pen mark. Needle 50 is introduced into the retropubic space paravesically along the posterior aspect of the pubic bone. (See FIG. 21.) Assistant continuously injects Xylocaine while needle 50 is driven. Assistant as well pulls the Foley catheter 91 to the contralateral side.

Figure 22:
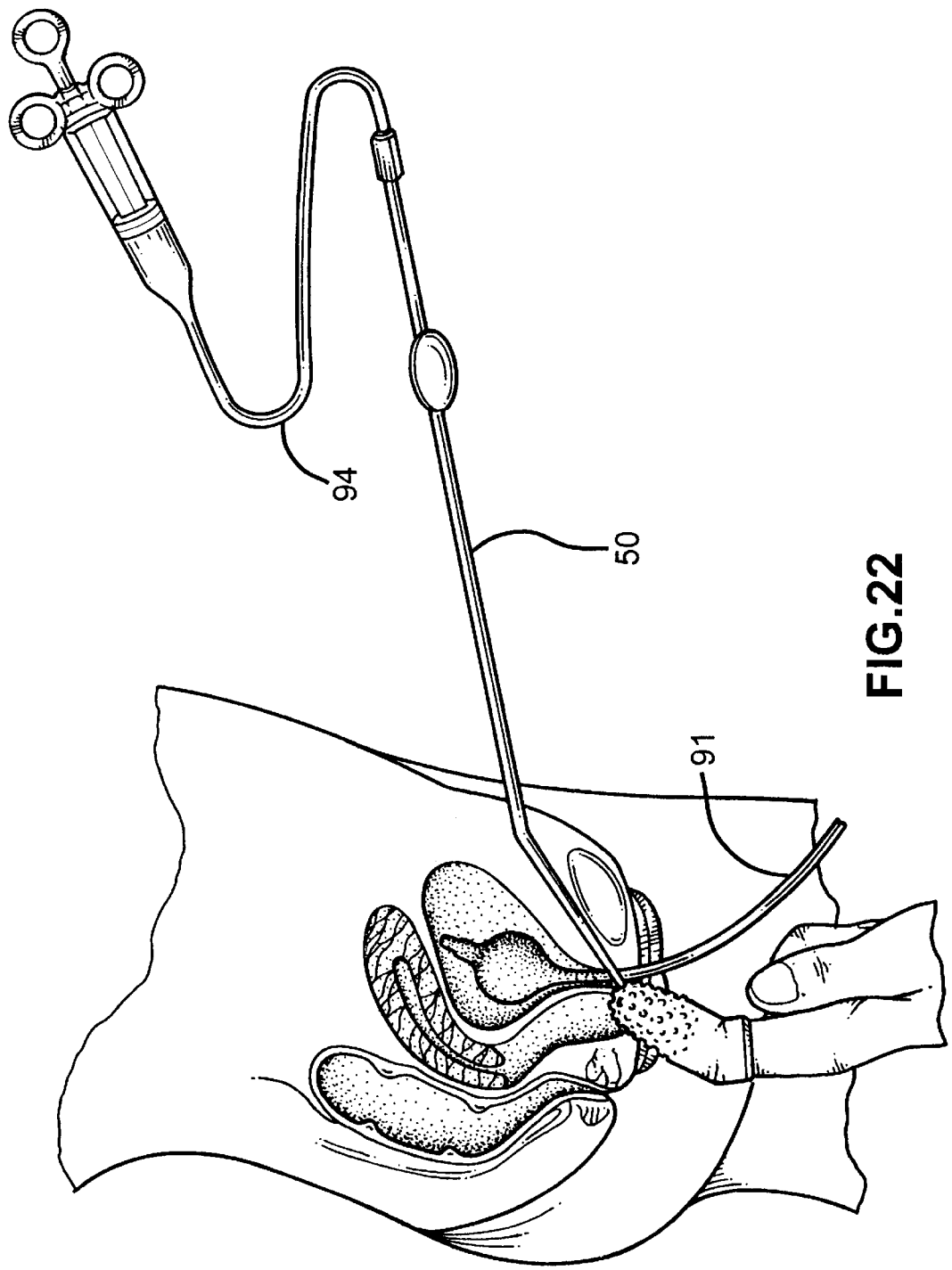

14. Index finger with thimble 96 is placed in the right side of the vagina lateral to the bladder neck and pushed upwardly behind the pubis. Needle 50 is guided over thimble 96 until needle 50 emerges through the vagina. (See FIG. 22.)

15. Disconnect needle 50 from tubing 94.

16. Steps 11 through 14 are repeated on the contralateral side.

17. Catheter 91 is removed and cystoscopy is performed with a 70-degree lens to rule out bladder perforation.

18. Foley catheter 91 is placed as in step 6.

Figure 23:
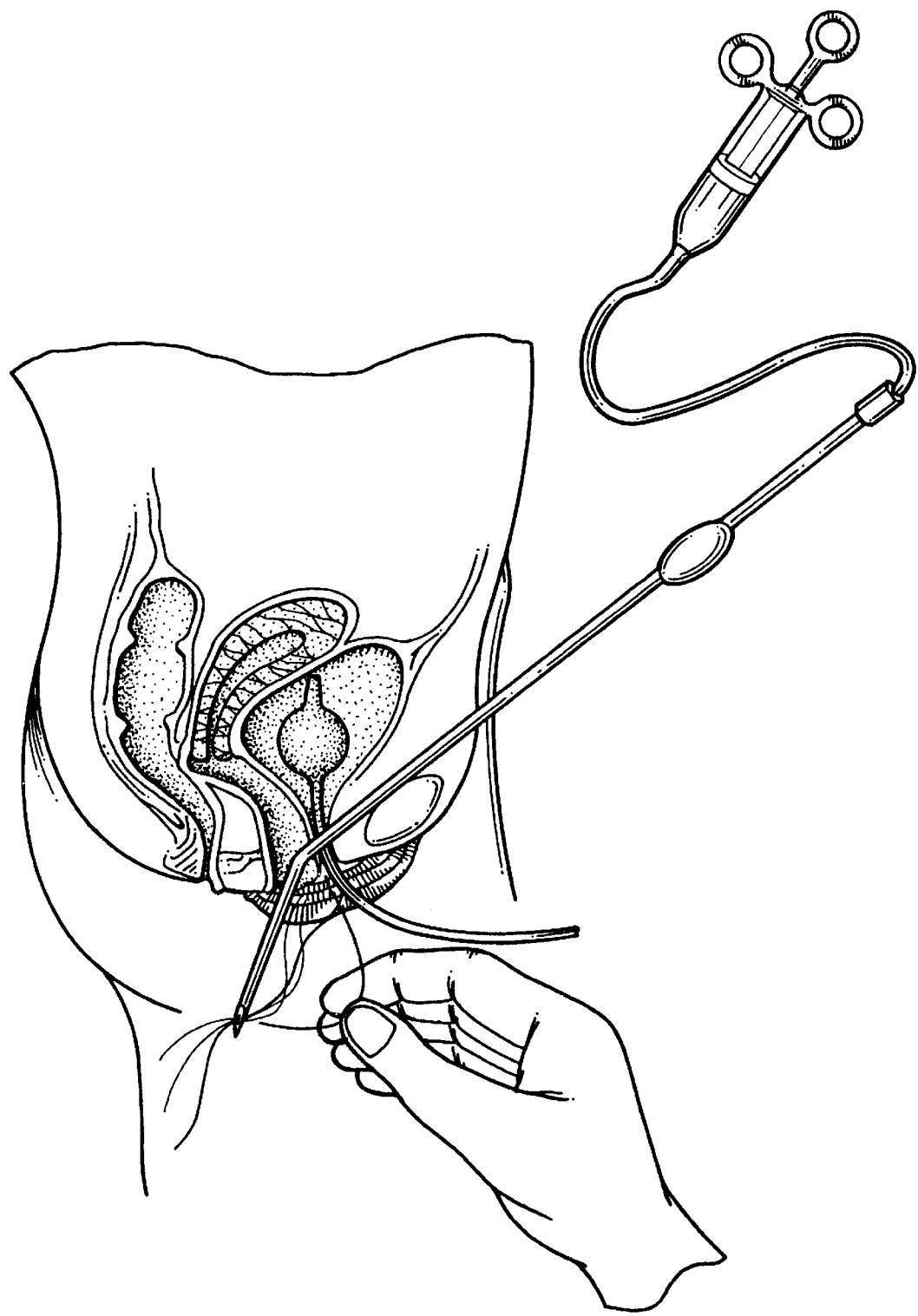

19. Sutures from both the curved and straight Kelly clamps are passed through hole 60 in needle 50 on both sides of the patient. (See FIG. 23.)

Figure 24:
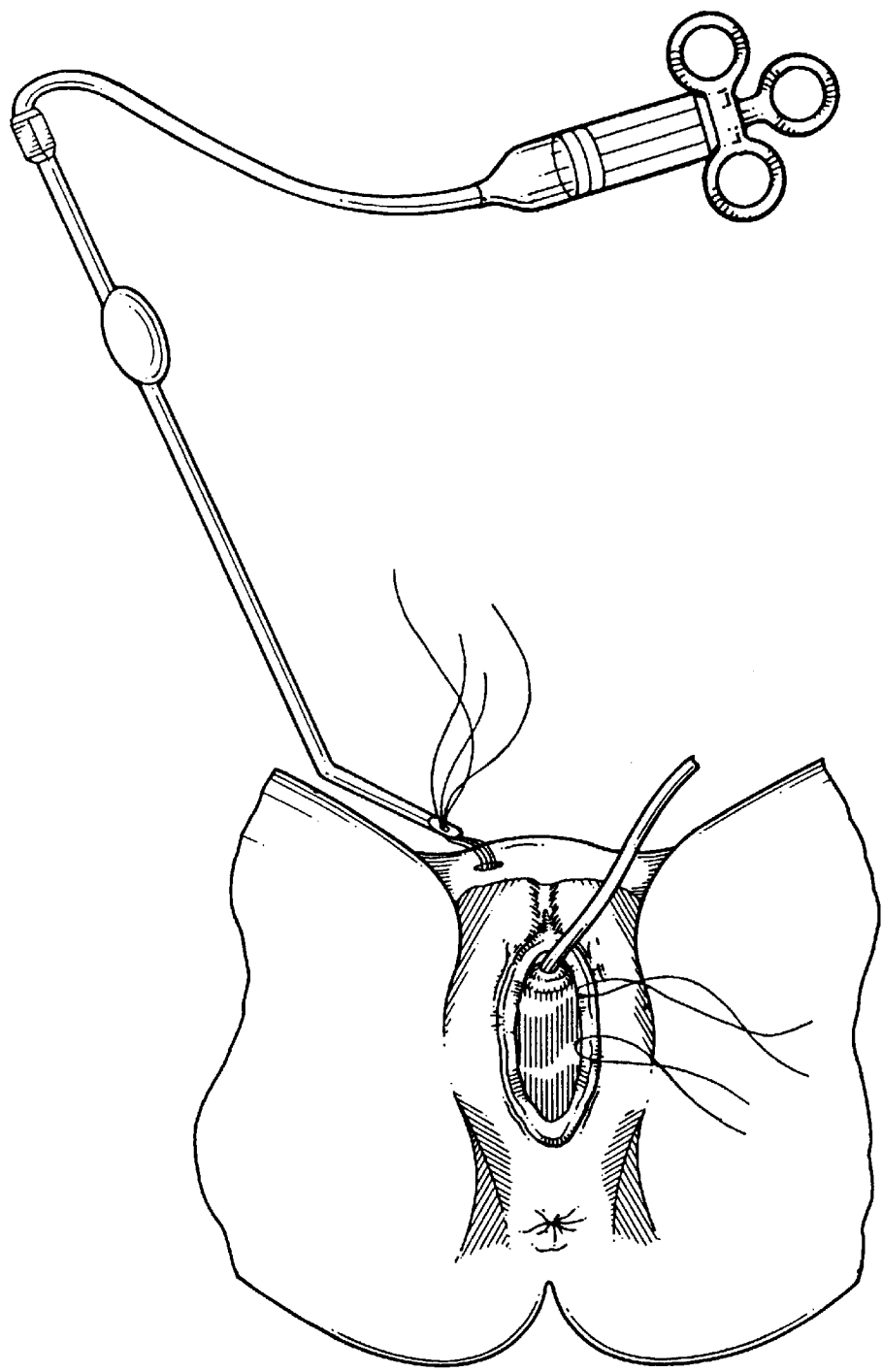
Figure 25:
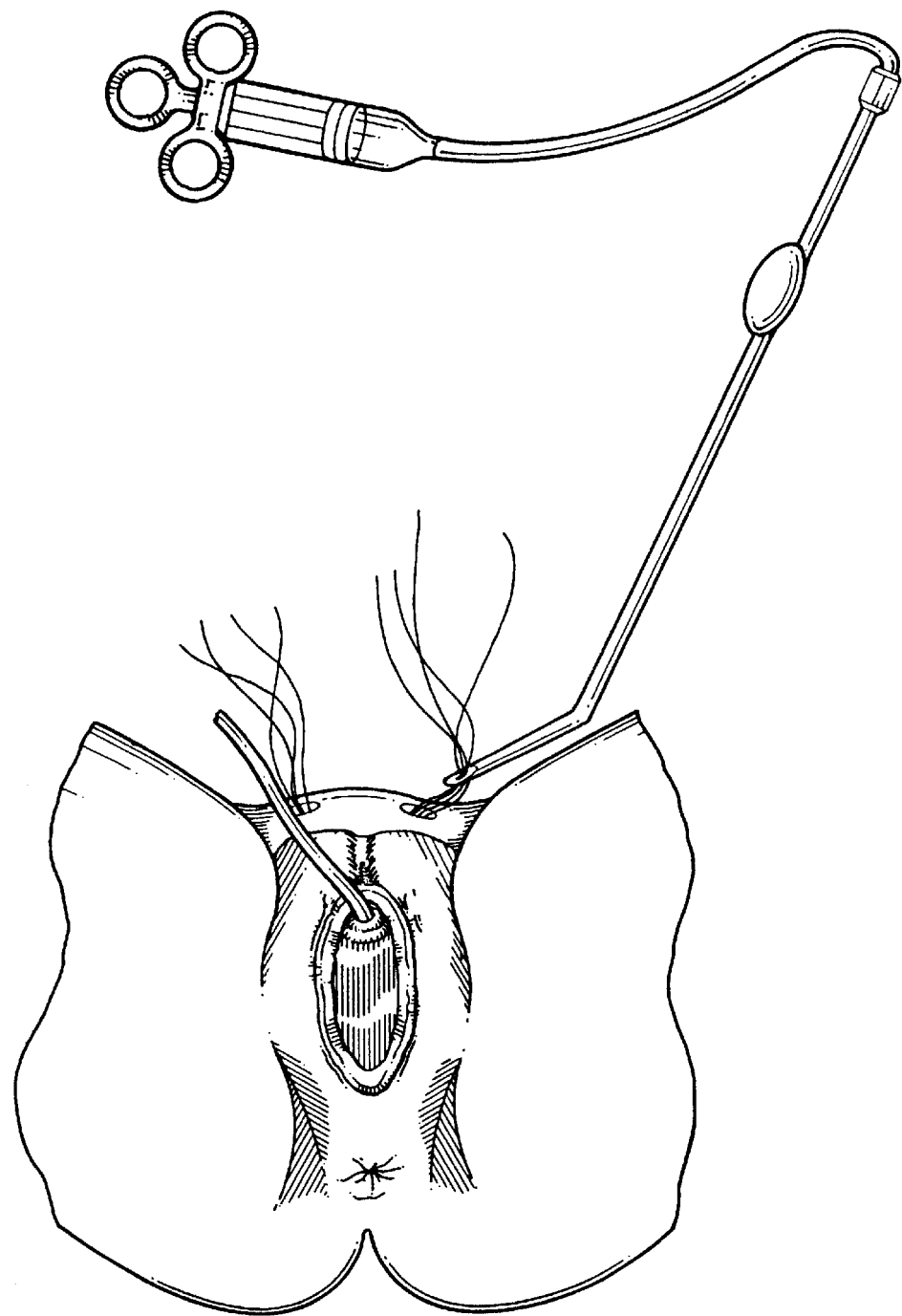

20. Needles 50 are pulled back slowly along the posterior aspect of the pubis until sutures are pulled through the anterior abdominal wall. (See FIGS. 24 and 25.)

21. Needle 50 is removed. On both sides crush marked suture is grasped with the curved Kelly clamp and unmarked suture is grasped with the straight Kelly clamp.

22. Steps 11 and 12 are repeated with needle 50'.

Figure 26:
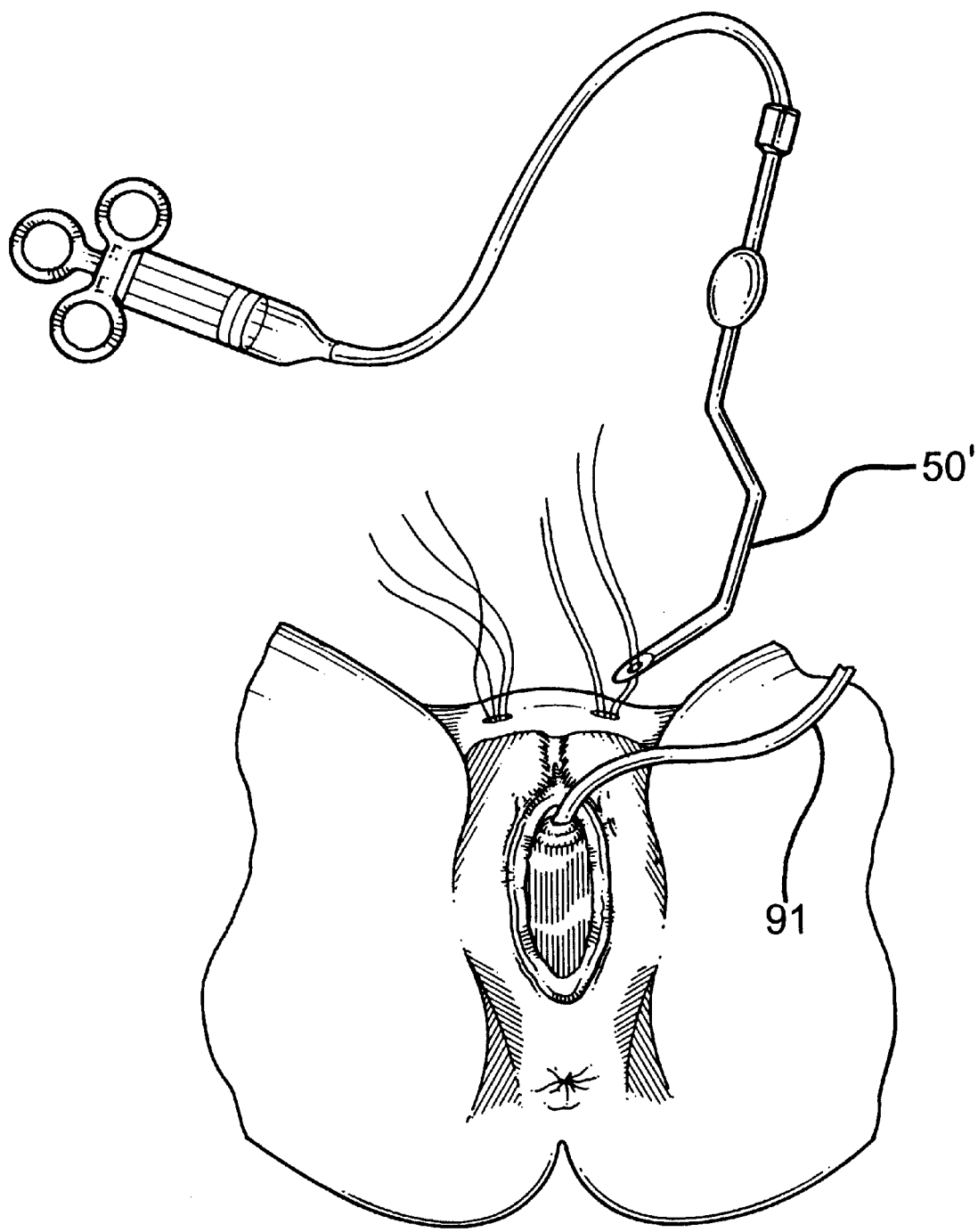

23. Release one arm of the left marked and unmarked suture and thread through hole 60' in needle 50'. Hold the other suture arms with curved and straight Kelly clamps. (See FIG. 26.)

24. Introduce needle 50' into the left skin puncture site. Continuously injecting Xylocaine drive needle 50' pointing downwardly then laterally just above the fascia and finally upwardly until needle 50' emerges through the right skin puncture site.

25. Release the suture from needle 50'.

Figure 27:
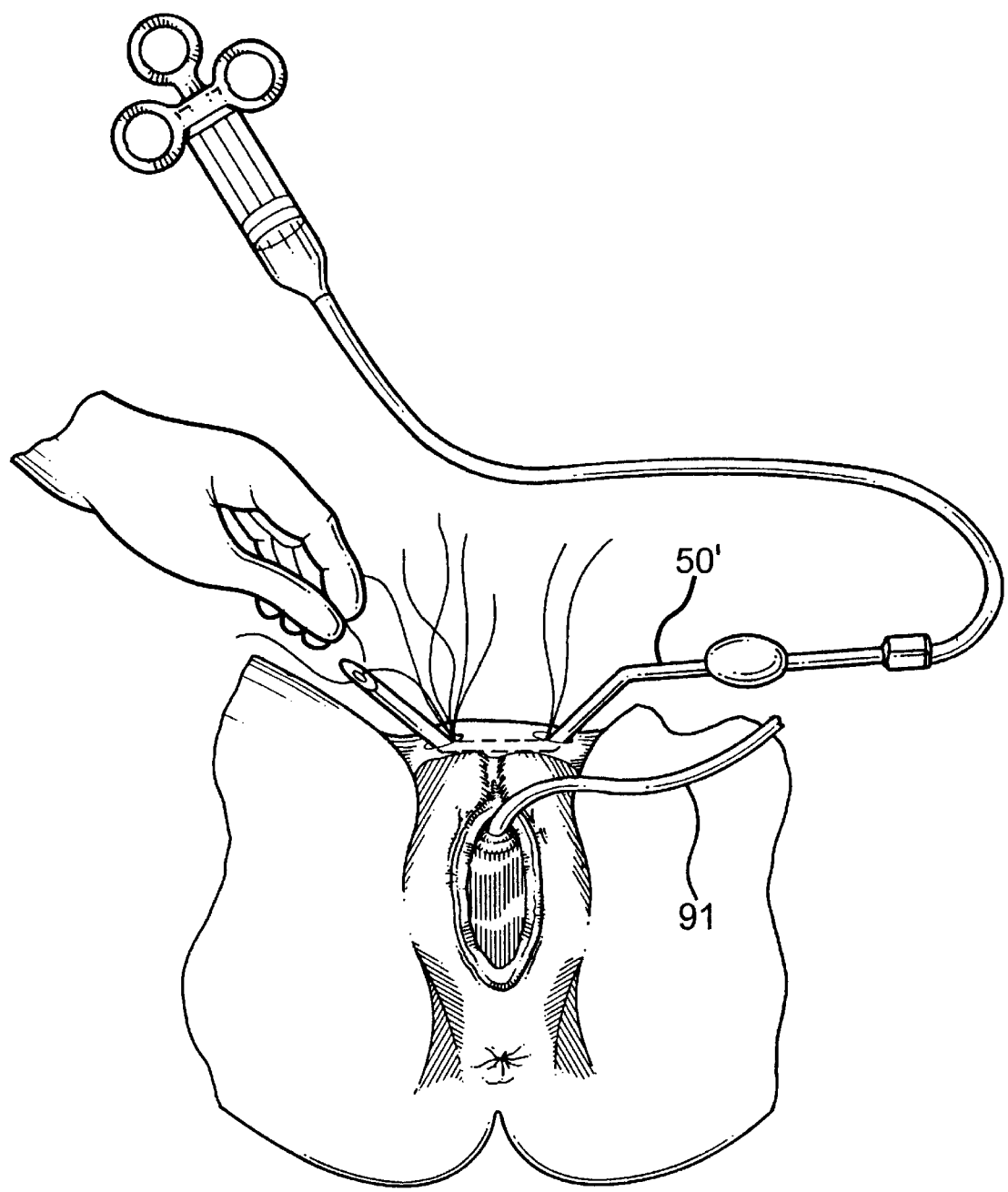

26. Release one arm of the right marked and unmarked suture and thread through hole 60' in needle 50'. Hold the other suture arms with curved and straight Kelly clamps along with the remaining left marked and unmarked suture arms. (See FIG. 27.)

27. Pull needle 50' back until suture emerges through the left puncture site. Release suture from needle 50' and hold the released suture with left marked and unmarked sutures using curved and straight Kelly clamps.

28. On both sides release Kelly clamps one at a time, apply slight traction on the sutures and reapply the Kelly clamps.

29. Assistant elevates the bladder neck by pushing anterior vaginal wall upwardly behind the pubis with fingers.

Figure 28:
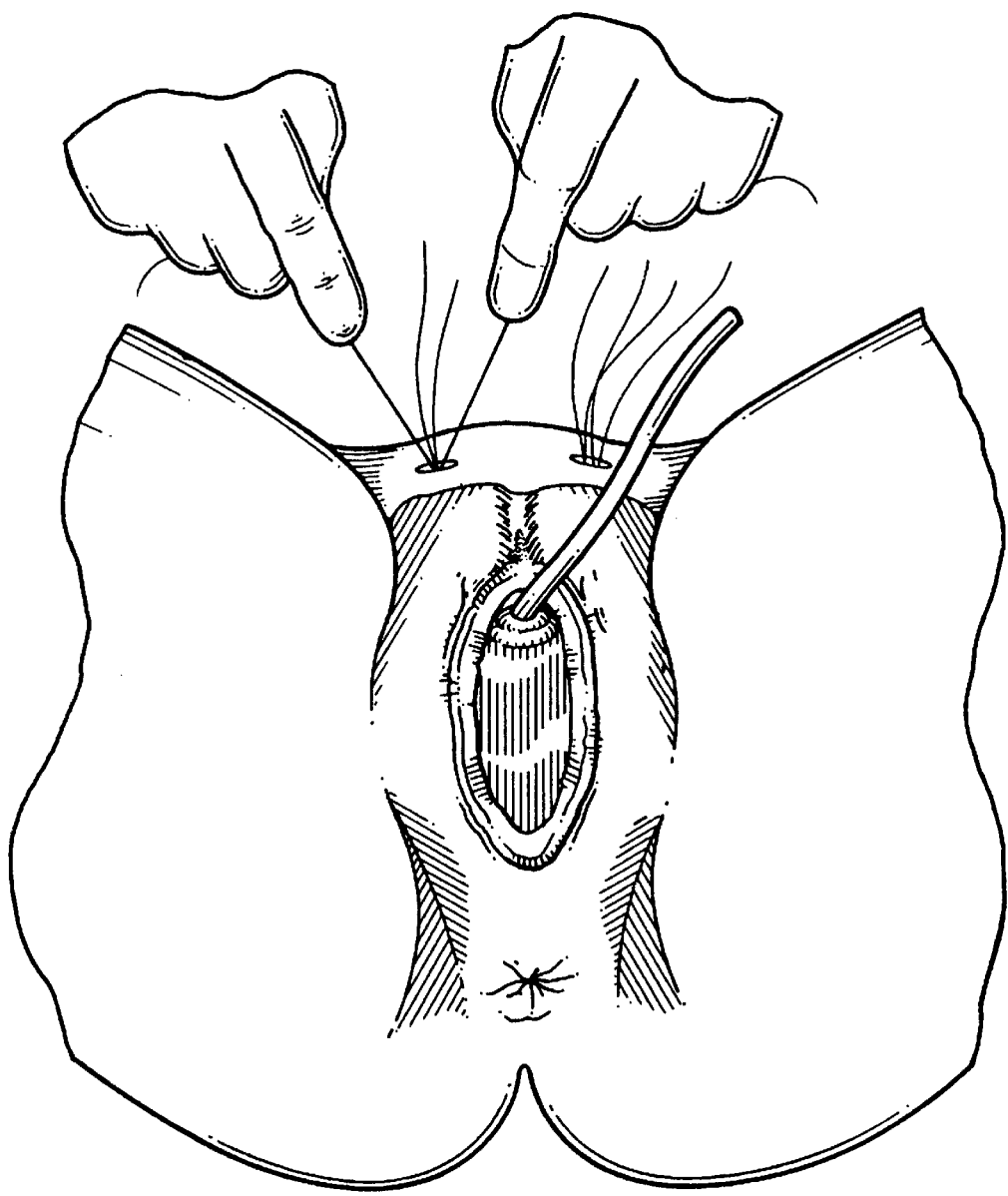

30. When bladder neck is in normal anatomical position, elevated by assistant's fingers, tie the sutures on both sides releasing each Kelly clamp with 8 knots into the skin puncture sites and cut the sutures right above the knots. (See FIG. 28.)

31. Lift the edges of the puncture sites bilaterally with Edson forceps and allow the knots to retract.

32. Apply sterile strips on puncture sites.

33. Clamp on the Foley catheter 91 is now removed. Patient is transferred to the recovery area with urinary drainage bag. Foley catheter 91 is removed before transfer if patient is prescribed intermittent self-catheterization.

Urethropexy

1. Prep and drape the patient in usual fashion in low lithotomy position. Drain the bladder.

2. Place a dot with marking pen 4 cm lateral from the midline on both sides just above the edge of the pubis.

3. Apply 1% Xylocaine jelly in the urethra and bladder.

4. Place a 4 inch×4 inch gauze pad soaked with 1% Xylocaine jelly in anterior portion of the vagina and remove after a few minutes.

5. Insert a weighted speculum to depress the posterior vagina.

6 Insert a 20 French Foley catheter 91 with 30 cc balloon, inflate and clamp.

7. Inject 1 cc of 1% Xylocaine into the skin at pen marks on both sides above the pubis.

8. Inject 1 cc of 1% Xylocaine on both sides 1 cm lateral at the level of the bladder neck.

9. Place a 3 loop suture 1 cm lateral at the level of distal ⅓ of urethra on both sides using a #1 Novafil on CT1 needle (or similar permanent suture) through the entire thickness of the vagina. Do not tie the knot. Hold the suture with straight Kelly clamps. (See FIG. 9.)

10. Fill a 15 cc syringe 93 with 1% Xylocaine. Attach syringe 93 to needle assembly 50 with small IV extension tubing 94 in a conventional manner.

11. Drain needle 50 to remove the air.

12. Thumbpiece 68 on needle 50 is firmly grasped, angled and directed towards the posterior pubis at the right pen mark. Needle 50 is introduced into the retropubic space paravesically along the posterior aspect of the pubic bone. (See FIG. 10.) Assistant continuously injects Xylocaine while needle 50 is driven. Assistant as well pulls the Foley catheter 91 to the contralateral side.

13. Index finger with thimble 96 is placed in the right side of vagina lateral to the bladder neck and pushed upwardly behind the pubis. Needle 50 is guided over thimble 96 until needle 50 emerges through the vagina. (See FIGS. 10–12.)

14. Disconnect needle 50 from tubing 94.

15. Steps 10 through 14 are repeated on the contralateral side.

16. Catheter 91 is removed and cystoscopy is performed with a 70-degree lens to rule out bladder perforation.

17. Foley catheter 91 is placed as in step 6.

18. Suture from the straight Kelly clamps is passed through hole 60 in needle 50 on both sides of the patient. (See FIG. 13.)

19. Needles 50 are pulled back slowly along the posterior aspect of the pubis until sutures are pulled through the anterior abdominal wall. (See FIGS. 14 and 15.)

20. Needle 50 is removed and suture grasped with straight Kelly clamp on both sides.

21. Steps 10 and 11 are repeated with needle assembly 50'.

22. Release one arm of the left suture and thread through hole 60' in needle 50'. (See FIG. 16.) Hold the other suture arm with a straight Kelly clamp.

23. Introduce needle 50' into the left skin puncture site. Continuously injecting Xylocaine drive needle 50' pointing downwardly then laterally just above the fascia and finally upwardly until needle 50' emerges through the right skin puncture site. (See FIG. 17.)

24. Release the suture from needle 50'.

25. Release one arm of the right suture and thread through hole 60' in needle 50'. (See FIG. 17.) Hold the other suture arm with the straight Kelly clamp along with the remaining left suture arm.

26. Pull needle 50' back until suture emerges through the left puncture site. Release the right suture from needle 50' and hold the right suture with left straight Kelly clamp.

27. Release Kelly clamps, apply slight traction on the sutures on both sides and reapply the Kelly clamps.

28. Assistant elevates the patient's distal urethra by pushing the anterior vaginal wall upwardly behind the pubis with fingers.

29. When the distal urethra is in normal anatomical position, elevated by assistant's fingers, tie the sutures on both sides with 8 knots into the skin puncture sites (see FIGS. 18 and 19) and cut the sutures right above the knots.

30. Lift the edges of the puncture sites bilaterally with Edson forceps and allow the knots to retract.

31. Apply sterile strips on puncture sites.

32. Clamp on the Foley catheter 91 is now removed. Patient is transferred to the recovery area with urinary drainage bag. Foley catheter 91 is removed before transfer if patient is prescribed intermittent self-catheterization.

Uteropexy

Uterine Suspension for Uterine Prolapse

Labor during childbirth and menopause among other conditions can lead to defects and weakening of the support structures of the uterus leading to uterine prolapse along with the weakening of the support structures of the bladder and the urethra. Suspension of the uterus in incontinence patients with uterine prolapse improves the outcome of the incontinence procedure.

1. Prep and drape the patient in usual fashion in low lithotomy position. Drain the bladder.

2. Place a dot with marking pen 4 cm lateral from the midline on both sides just above the edge of the pubis.

3. Apply 1% Xylocaine jelly in the urethra and bladder.

4. Place a 4 inch×4 inch gauze pad soaked with 1% Xylocaine jelly in anterior portion of the vagina and remove after a few minutes.

5. Insert a weighted speculum to depress the posterior vagina.

6. Insert a 20 French Foley catheter 91 with 30 cc balloon, inflate and clamp.

7. Inject 1 cc of 1% Xylocaine into the skin at pen marks on both sides above the pubis.

8. About 3 cc of local anesthetic is injected into the uterine wall at the level of the cardinal ligament or uterosacral ligament on both sides.

9. 5–10 cc of local anesthetic is infiltrated submucosally from the ligament to the urethrovesical junction on both sides.

10. Using #1 permanent sutures (Prolene or Novafil) a two to three loop submucosal suture is placed around the ligament (cardinal or uterosacral). To place a submucosal suture the suture needle is introduced into the uterine wall (first puncture site) and exited. After the exit, the needle is introduced back into the exit site, advanced submucosally and delivered through the first puncture site. This allows the sutures to be buried entirely into the tissue.

11. If combining with a different procedure (bladder suspension, etc.) for later identification a crush mark using a needle holder is placed about 2 cm from the tip of each suture arm.

12. Needle is removed from the suture.

13. A free needle is used to pass both arms of the suture underneath the mucosa from the ligament to the urethrovesical angle.

14. Both arms of the suture are held with a clamp.

15. Steps 10–13 are performed on the contralateral side. (Steps 10–13 are performed on both sides.)

16. Fill a 15 cc syringe 93 with 1% Xylocaine. Attach syringe 93 to needle assembly 50 with small IV extension tubing 94 in a conventional manner.

17. Drain needle 50 to remove the air.

18. Thumbpiece 68 on needle 50 is firmly grasped, angled and directed towards the posterior pubis at the right pen mark. Needle 50 is introduced into the retropubic space paravesically along the posterior aspect of the pubic bone. (See FIG. 10.) Assistant continuously injects Xylocaine while needle 50 is driven. Assistant as well pulls the Foley catheter to the contralateral side.

19. Index finger with a thimble 96 is placed in the right side of vagina lateral to the bladder neck and pushed upwardly behind the pubis. Needle 50 is guided over thimble 96 until it emerges through the vagina. (See FIGS. 10–12.)

20. Disconnect needle 50 from tubing 94.

21. Steps 16 through 20 are repeated on the contralateral side.

22. Catheter 91 is removed and cystoscopy is performed with a 70-degree lens to rule out bladder perforation.

23. catheter 91 is placed as in step 6.

24. Suture from the straight Kelly clamps is passed through hole 60 in needle 50 on both sides of the patient. (See FIG. 13.)

25. Needles 50 are pulled back slowly along the posterior aspect of the pubis until sutures are pulled through the anterior abdominal wall. (See FIGS. 14 and 15)

26. Needle 50 is removed and suture grasped with straight Kelly clamp on both sides.

27. Steps 16 and 17 are repeated with needle assembly 50'.

28. Release one arm of the left suture and thread through hole 60 in needle 50'. (See FIG. 16.) Hold the other suture arm with a straight Kelly clamp.

29. Introduce needle 50' into the left skin puncture site. Continuously injecting Xylocaine drive needle 50' pointing downwardly then laterally just above the fascia and finally upwardly until needle 50' emerges through the right skin puncture site. (See FIG. 17.)

30. Release the suture from needle 50'.

31. Release one arm of the right suture and thread through hole 60' in needle 50'. (See FIG. 17.) Hold the other suture arm with the straight Kelly clamp along with the remaining left suture arm.

32. Pull needle 50' back until suture emerges through the left puncture site. Release the right suture from needle 50' and hold the right suture with left straight Kelly clamp.

33. Release Kelly clamps, apply slight traction on the sutures on both sides and reapply the Kelly clamps.

34. Assistant elevates the patient's uterus by pushing the anterior vaginal wall upwardly behind the pubis with fingers.

35. When uterus is in normal anatomical position, elevated by assistant's fingers, tie the sutures on both sides with 8 knots into the skin puncture sites (see FIGS. 18 and 19) and cut the sutures right above the knots.

36. Lift the edges of the puncture sites bilaterally with Edson forceps and allow the knots to retract.

37. Apply sterile strips on puncture sites.

38. Clamp on the Foley catheter 91 is now removed. Patient is transferred to the recovery area with urinary drainage bag. Foley catheter 91 is removed before transfer if the patient is prescribed intermittent self-catheterization.

It should be understood that a permanent suture like Prolene can be used instead of Novafil and that other local anesthetic, instead of Xylocaine, can be used in the procedures described.

The invention in its broader aspects is not limited to the specific details shown and described, and departures may be made from such details without departing from the principles of the invention and without sacrificing its chief advantages.

What is claimed is:

1. A suturing needle assembly for enabling simultaneous passage of suture and introduction of local anesthetic into body tissue, said assembly comprising:

a hollow needle body defining an interior passageway and further defining first and second ends having first and second openings therein, respectively, in fluid communication with said passageway;

said first end further defining a third opening therein for removably receiving a suture;

means connected to said second end for removably attaching said needle assembly to a source of local anesthetic;

said first end being bevelled with respect to said needle body to form a bevelled end surface; and said third opening extending through said bevelled end surface.

2. An assembly as in claim 1 further including means attached to said needle body for enhancing a user's grip of said assembly during use.

3. An assembly as in claim 2 wherein said needle body defines a first substantially straight portion adjacent to said first end and a second substantially straight portion connected to said first straight portion and adjacent to said second end, said first and second straight portions defining an angle of substantially one hundred forty-five degrees therebetween.

4. An assembly as in claim 3 wherein said angle is from one hundred ten degrees to one hundred eighty degrees.

5. An assembly as in claim 2 wherein said needle body defines a first substantially straight portion adjacent to said first end; a second substantially straight portion adjacent to said second end; a third substantially straight portion connected to said first straight portion; and a fourth substantially straight portion connected between said second and third straight portions defining first and second angles of substantially one hundred forty-five degrees with each of said second and third straight portions, respectively, and said first and third straight portions defining a third angle of substantially one hundred thirty-five degrees therebetween.

6. An assembly as in claim 5 wherein said first and second angles are from one hundred fifteen degrees to one hundred seventy-five degrees and wherein said third angle is from one hundred five degrees to one hundred sixty-five degrees.

7. An assembly as in claim 6 wherein said second straight portion defines an extended imaginary straight centerline there through which intersects said first straight portion.

8. A method of simultaneously passing suture and introducing local anesthetic into body tissue, said method comprising the steps of:

providing the suturing needle assembly of claim 1;

positioning said suture into and through said third opening;

attaching said source of local anesthetic to said needle assembly; and introducing said first end of said needle assembly, said suture and said local anesthetic substantially simultaneously into said body tissue.

9. The method of claim 8 wherein said step of introducing said local anesthetic into said body tissue further includes the step of:
passing said local anesthetic from said source of local anesthetic through said second opening, through said interior passageway of said hollow needle body, and through said first opening into said body tissue.

10. A method of suspending a bladder neck of a patient, comprising the steps of:
placing first and second sutures at first and second locations, respectively, at the level of the bladder neck through the entire thickness of the vagina on both sides from the midline of the patient's body;
holding the first and second sutures;
simultaneously introducing and driving a first said needle body of a first said needle assembly of claim 3 into a third location, which is a predetermined distance toward a first side from the midline of the patient's body just above the edge of the pubis, and into the retropubic space paravesically along the posterior aspect of the pubic bone and introducing local anesthetic through said first needle body as said first needle body is driven;
guiding said first needle body until it emerges through the vagina;
disconnecting a first said source of local anesthetic from said first needle assembly;
simultaneously introducing and driving a second said needle body of a second said needle assembly of claim 3 into a fourth location a predetermined distance toward a second side from the midline of the patient's body just above the edge of the pubis and into the retropubic space paravesically along the posterior aspect of the pubic bone and introducing local anesthetic through said second needle body as said second needle body is driven;
guiding said second needle body until it emerges through the vagina;
disconnecting a second said source of local anesthetic from said second needle assembly;
passing said first and second sutures through said third openings in said first and second needle bodies, respectively;
pulling said first and second needle bodies back along the posterior aspect of the pubis until said first and second sutures are pulled through the anterior abdominal wall of the patient;
removing said first and second needle bodies from said first and second sutures, respectively;
grasping said first and second sutures;
releasing a first portion of said first suture and threading said first suture portion through said third opening of a first said needle body of a first said needle assembly of claim 5;
holding a second portion of said first suture;
introducing said first needle body of said first needle assembly of claim 5 into a third location on the patient's body a predetermined distance laterally from the midline above the edge of the pubis;
simultaneously introducing said local anesthetic through said first needle body of said first needle assembly of claim 5 and driving said first needle body of said first needle assembly of claim 5 downwardly and then laterally just above the fascia and then upwardly until said last-mentioned needle body emerges through the skin at a fourth location on the patient's body a predetermined distance laterally from the midline above the edge of the pubis;
releasing said first suture from said last-mentioned needle body;
releasing a first portion of said second suture and threading said last-mentioned first suture portion through said third opening of said first needle body of said first needle assembly of claim 5;
holding a second portion of said second suture together with said first portion of said first suture;
pulling said last-mentioned needle body backwardly until said second suture emerges through said third location on the patient's body;
releasing said second suture from said last-mentioned needle body and holding said second suture;
releasing said first and second sutures;
applying traction on said first and second sutures and then reholding said first and second sutures;
elevating the bladder neck to a normal anatomical position;
tieing said first and second sutures into knots when said bladder neck is elevated to a normal anatomical position; and
cutting said first and second sutures above said knots.

11. A method as in claim 10 wherein said first and second locations are each substantially one centimeter laterally from the midline of the patient's body.

12. A method of bladder neck and urethral suspension of a patient, comprising the steps of:
placing first and second sutures at first and second locations, respectively, at the level of the bladder neck through the entire thickness of the vagina on both sides from the midline of the patient's body;
holding the first and second sutures;
placing third and fourth sutures at third and fourth locations, respectively, at the level of proximal one-third of the urethra on both sides from the midline of the patient's body through the entire thickness of the vagina;
marking ends of said third and fourth sutures for later identification;
holding said third and fourth sutures;
simultaneously introducing and driving a first said needle body of a first said needle assembly of claim 5 into a fifth location, which is a predetermined distance toward a first side from the midline of the patient's body just above the edge of the pubis, and into the retropubic space paravesically along the posterior aspect of the pubic bone and introducing local anesthetic through said first needle body as said first needle body is driven;
guiding said first needle body until it emerges through the vagina;
disconnecting a first said source of local anesthetic from said first needle assembly;
simultaneously introducing and driving a second said needle body of a second said needle assembly of claim 5 into a sixth location a predetermined distance toward a second side from the midline of the patient's body just above the edge of the pubis and into the retropubic space paravesically along the posterior aspect of the pubic bone and introducing local anesthetic through said second needle body as said second needle body is driven;

guiding said second needle body until it emerges through the vagina;

disconnecting a second said source of local anesthetic from said second needle assembly;

passing said first and third sutures through said third opening in said first needle body;

passing said second and fourth sutures through said third opening in said second needle body;

pulling said first and second needle bodies back along the posterior aspect of the pubis until said first, second, third and fourth sutures are pulled through the anterior abdominal wall of the patient;

removing said first needle body from said first and third sutures;

removing said second needle body from said second and fourth sutures;

grasping said first, second, third and fourth sutures;

releasing first portions of said first and third sutures and threading said first and third suture portions through said third opening of a first said needle body of a first said needle assembly of claim 5;

holding second portions of said first and third sutures;

introducing said first needle body of said first needle assembly of claim 5 into said fifth location on the patient's body a predetermined distance laterally from the midline above the edge of the pubis;

simultaneously introducing said local anesthetic through said first needle body of said first needle assembly of claim 5 and driving said first needle body of said first needle assembly of claim 5 downwardly and then laterally just above the fascia and then upwardly until said last-mentioned needle body emerges through the skin at said sixth location on the patient's body a predetermined distance laterally from the midline above the edge of the pubis;

releasing said first and third sutures from said last-mentioned needle body;

releasing first portions of said second and fourth sutures and threading said last-mentioned first suture portions through said third opening of said first needle body of said first needle assembly of claim 5;

holding second portions of said second and fourth sutures together with said first portions of said first and third sutures;

pulling said last-mentioned needle body backwardly until said second and fourth sutures emerge through said fifth location on the patient's body;

releasing said second and fourth sutures from said last-mentioned needle body and holding said second and fourth sutures;

releasing said first, second, third and fourth sutures;

applying traction on said first, second, third and fourth sutures and then reholding said first, second, third and fourth sutures;

elevating the bladder neck to a normal anatomical position;

tieing said first, second, third and fourth sutures into knots when said bladder neck is elevated to a normal anatomical position; and cutting said first, second, third and fourth sutures above said knots.

13. A method as in claim 12 wherein said first and second locations are each substantially one centimeter laterally from the midline of the patient's body.

14. A method of urethral suspension of a patient, comprising the steps of:

placing first and second sutures at first and second locations, respectively, at the level of proximal one-third of the urethra through the entire thickness of the vagina on both sides from the midline of the patient's body;

holding the first and second sutures;

simultaneously introducing and driving a first said needle body of a first said needle assembly of claim 3 into a third location, which is a predetermined distance toward a first side from the midline of the patient's body just above the edge of the pubis, and into the retropubic space paravesically along the posterior aspect of the pubic bone and introducing local anesthetic through said first needle body as said first needle body is driven;

guiding said first needle body until it emerges through the vagina;

disconnecting a first said source of local anesthetic from said first needle assembly;

simultaneously introducing and driving a second said needle body of a second said needle assembly of claim 5 into a fourth location a predetermined distance toward a second side from the midline of the patient's body just above the edge of the pubis and into the retropubic space paravesically along the posterior aspect of the pubic bone and introducing local anesthetic through said second needle body as said second needle body is driven;

guiding said second needle body until it emerges through the vagina;

disconnecting a second said source of local anesthetic from said second needle assembly;

passing said first and second sutures through said third openings in said first and second needle bodies, respectively;

pulling said first and second needle bodies back along the posterior aspect of the pubis until said first and second sutures are pulled through the anterior abdominal wall of the patient;

removing said first and second needle bodies from said first and second sutures, respectively;

grasping said first and second sutures;

releasing a first portion of said first suture and threading said first suture portion through said third opening of a first said needle body of a first said needle assembly of claim 5;

holding a second portion of said first suture;

introducing said first needle body of said first needle assembly of claim 5 into a third location on the patient's body a predetermined distance laterally from the midline above the edge of the pubis;

simultaneously introducing said local anesthetic through said first needle body of said first needle assembly of claim 5 and driving said first needle body of said first needle assembly of claim 5 downwardly and then laterally just above the fascia and then upwardly until said last-mentioned needle body emerges through the skin at a fourth location on the patient's body a predetermined distance laterally from the midline above the edge of the pubis;

releasing said first suture from said last-mentioned needle body;

releasing a first portion of said second suture and threading said last-mentioned first suture portion through said third opening of said first needle body of said first needle assembly of claim 5;

holding a second portion of said second suture together with said first portion of said first suture;

pulling said last-mentioned needle body backwardly until said second suture emerges through said third location on the patient's body;

releasing said second suture from said last-mentioned needle body and holding said second suture;

releasing said first and second sutures;

applying traction on said first and second sutures and then reholding said first and second sutures;

elevating the distal urethra to a normal anatomical position;

tieing said first and second sutures into knots when said distal urethra is elevated to a normal anatomical position; and cutting said first and second sutures above said knots.

15. A method as in claim 14 wherein said first and second locations are each substantially one centimeter laterally from the midline of the patient's body.

16. A method of uterine suspension for uterine prolapse of a patient, comprising the steps of:

placing first and second submucosal sutures at first and second locations, respectively, around a predetermined ligament;

passing said first and second sutures underneath the mucosa from said ligament to the urethrovesical angle;

holding the first and second sutures;

simultaneously introducing and driving a first said needle body of a first said needle assembly of claim 5 into a third location, which is a predetermined distance toward a first side from the midline of the patient's body just above the edge of the pubis, and into the retropubic space paravesically along the posterior aspect of the pubic bone and introducing local anesthetic through said first needle body as said first needle body is driven;

guiding said first needle body until it emerges through the vagina;

disconnecting a first said source of local anesthetic from said first needle assembly;

simultaneously introducing and driving a second said needle body of a second said needle assembly of claim 3 into a fourth location a predetermined distance toward a second side from the midline of the patient's body just above the edge of the pubis and into the retropubic space paravesically along the posterior aspect of the pubic bone and introducing local anesthetic through said second needle body as said second needle body is driven;

guiding said second needle body until it emerges through the vagina;

disconnecting a second said source of local anesthetic from said second needle assembly;

passing said first and second sutures through said third openings in said first and second needle bodies, respectively;

pulling said first and second needle bodies back along the posterior aspect of the pubis until said first and second sutures are pulled through the anterior abdominal wall of the patient;

removing said first and second needle bodies from said first and second sutures, respectively;

grasping said first and second sutures;

releasing a first portion of said first suture and threading said first suture portion through said third opening of a first said needle body of a first said needle assembly of claim 5;

holding a second portion of said first suture;

introducing said first needle body of said first needle assembly of claim 5 into a third location on the patient's body a predetermined distance laterally from the midline above the edge of the pubis;

simultaneously introducing said local anesthetic through said first needle body of said first needle assembly of claim 5 and driving said first needle body of said first needle assembly of claim 5 downwardly and then laterally just above the fascia and then upwardly until said last-mentioned needle body emerges through the skin at a fourth location on the patient's body a predetermined distance laterally from the midline above the edge of the pubis;

releasing said first suture from said last-mentioned needle body;

releasing a first portion of said second suture and threading said last-mentioned first suture portion through said third opening of said first needle body of said first needle assembly of claim 5;

holding a second portion of said second suture together with said first portion of said first suture;

pulling said last-mentioned needle body backwardly until said second suture emerges through said third location on the patient's body;

releasing said second suture from said last-mentioned needle body and holding said second suture;

releasing said first and second sutures;

applying traction on said first and second sutures and then reholding said first and second sutures;

elevating the uterus to a normal anatomical position;

tieing said first and second sutures into knots when said uterus is elevated to a normal anatomical position; and cutting said first and second sutures above said knots.

\* \* \* \* \*